United States Patent
Tabayashi et al.

(10) Patent No.: US 11,427,620 B2
(45) Date of Patent: Aug. 30, 2022

(54) MALARIA TRANSMISSION BLOCKING VACCINE

(71) Applicants: Hokusan Co. Ltd., Kitahiroshima (JP); National Institute of Advanced Industrial Science and Technology, Tokyo (JP); School Juridical Person The Kitasato Institute, Tokyo (JP)

(72) Inventors: Noriko Tabayashi, Kitahiroshima (JP); Toru Gotanda, Kitahiroshima (JP); Hanae Sasaki, Kitahiroshima (JP); Noriko Itchoda, Kitahiroshima (JP); Uiko Kagaya, Kitahiroshima (JP); Takeshi Matsumura, Sapporo (JP); Akira Ito, Sapporo (JP); Hiromi Ikadai, Sagamihara (JP)

(73) Assignees: Hokusan Co., Ltd., Kitahiroshima (JP); National Institute of Advanced Industrial Science and Technology, Tokyo (JP); School Juridical Person The Kitasato Institute, Tokyo (JP)

( * ) Notice: Subject to any disclaimer, the term of this patent is extended or adjusted under 35 U.S.C. 154(b) by 563 days.

(21) Appl. No.: 16/330,623

(22) PCT Filed: Sep. 4, 2017

(86) PCT No.: PCT/JP2017/031784
§ 371 (c)(1),
(2) Date: Mar. 5, 2019

(87) PCT Pub. No.: WO2018/043741
PCT Pub. Date: Mar. 8, 2018

(65) Prior Publication Data
US 2021/0292382 A1 Sep. 23, 2021

(30) Foreign Application Priority Data

Sep. 5, 2016 (JP) .............................. JP2016-173018

(51) Int. Cl.
*A61K 39/015* (2006.01)
*C07K 14/445* (2006.01)
*A61K 39/00* (2006.01)
*C12N 15/82* (2006.01)
*A61P 33/06* (2006.01)
*A61K 9/00* (2006.01)

(52) U.S. Cl.
CPC .......... *C07K 14/445* (2013.01); *A61K 9/0056* (2013.01); *A61K 39/015* (2013.01); *A61P 33/06* (2018.01); *C12N 15/8258* (2013.01); *A61K 2039/542* (2013.01); *A61K 2039/552* (2013.01)

(58) Field of Classification Search
None
See application file for complete search history.

(56) References Cited

FOREIGN PATENT DOCUMENTS

| EP | 1767639 A1 | 3/2007 |
|---|---|---|
| JP | 2003-277292 A | 10/2003 |
| WO | WO 2012/170125 A2 | 12/2012 |

OTHER PUBLICATIONS

Greenspan et al. Nature Biotechnology 17: 936-937, 1999.*
Rudinger J. In: Peptide Hormones. (Ed) JA Parsons, University Park Press, pp. 1-7, 1976.*
Skolnick et al. Trends in Biotechnology, 18: 34-39, 2000.*
Hewetson et al., An in vivo passive protection assay for the evaluation of immunity in AVA-vaccinated individuals. Vaccine. Aug. 5, 2008;26(33):4262-6. doi: 10.1016/j.vaccine.2008.05.068. Epub Jun. 12, 2008.
Srinivasan et al., PbCap380, a novel oocyst capsule protein, is essential for malaria parasite survival in the mosquito. Cell Microbiol. Jun. 2008;10(6):1304-12. doi: 10.1111/j.1462-5822.2008.01127.x. Epub Feb. 1, 2008.
Crompton et al., Advances and challenges in malaria vaccine development. (2010) J Clin Invest. 120(12):4168-78.
Genbank accession No. CDS46529, Nov. 23, 2015, Otto et al. 2 pages.
Genbank accession No. CDU21322, Nov. 23, 2015, Otto et al. 2 pages.
Gholizadeh, S., et al., Cloning, expression and transmission-blocking activity of anti-PvWARP, malaria vaccine candidate, in Anopheles stephensi mysorensis. Malar J. Jun. 11, 2010;9:158. 7 pages.
Itchoda et al., A plant-derived malaria transmission-blocking vaccine candidate induces immunological memory in orally immunized mice. Abstracts of the Annual Meeting of the Society for Biotechnology, Japan, 2015, vol. 67:326, 3P-221. 4 pages.
Kimura et al., PbCAP494 of malaria parasite oocyst-wall proteins is involved in the early stage of oocyst formation. The Japanese Society of Veterinary Science, Aug. 2016;159(CO-10):333. 4 pages.
Sasaki et al., Morphological analysis of malaria parasite deficient in the oocyst wall protein PbCap93 gene. The Japanese Society of Veterinary Science, Aug. 2016;159(CO-11):333. 4 pages.

(Continued)

*Primary Examiner* — Sarvamangala Devi
(74) *Attorney, Agent, or Firm* — Wolf, Greenfield & Sacks, P.C.

(57) ABSTRACT

It is an object of the present invention to provide a transmission-blocking vaccine using an immunogenic protein which is specifically expressed in the oocyst stage of malaria parasites or a peptide fragment thereof, and an oral transmission-blocking vaccine capable of immunizing various animals involved in the malaria infectious cycle with such a vaccine.
The present invention relates to a malaria transmission-blocking vaccine for oral administration containing an immunogenic protein derived from malaria parasite which is specifically expressed in the oocyst stage of malaria parasites or a peptide fragment thereof, and a method of blocking the transmission of malaria using the same.

6 Claims, 6 Drawing Sheets

Specification includes a Sequence Listing.

(56) References Cited

OTHER PUBLICATIONS

Sasaki et al., Plasmodium berghei Cap93, a novel oocyst capsule-associated protein, plays a role in sporozoite development. Parasit Vectors. Aug. 25, 2017;10(1):399. 9 pages.
PCT/JP2017/031784, Oct. 10, 2017, International Search Report and Written Opinion and English Translation thereof.
PCT/JP2017/031784, Mar. 14, 2019, International Preliminary Report on Patentability and English Translation thereof.
EP 17846744.5, Apr. 17, 2020, Extended European Search Report.

* cited by examiner

[Figure 1]
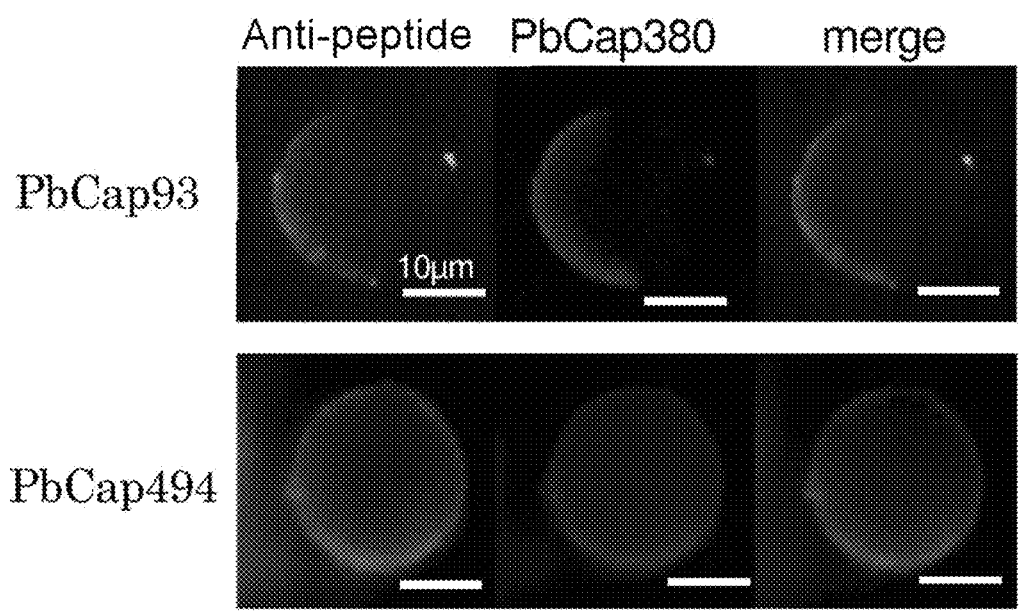
\* Oocysts of 15 days after blood-fed

[Figure 2]
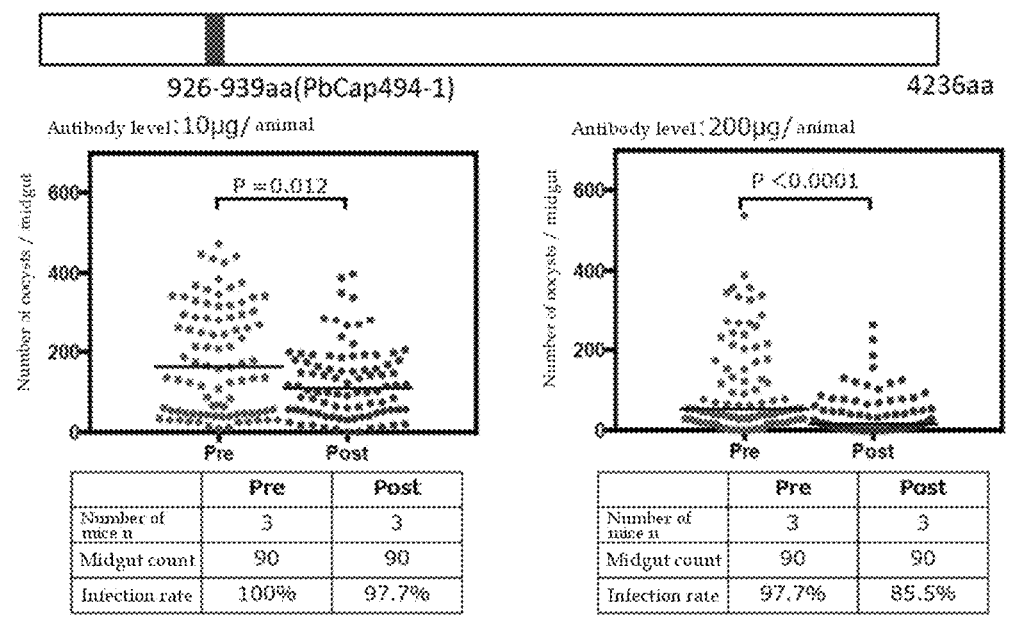

[Figure 3]
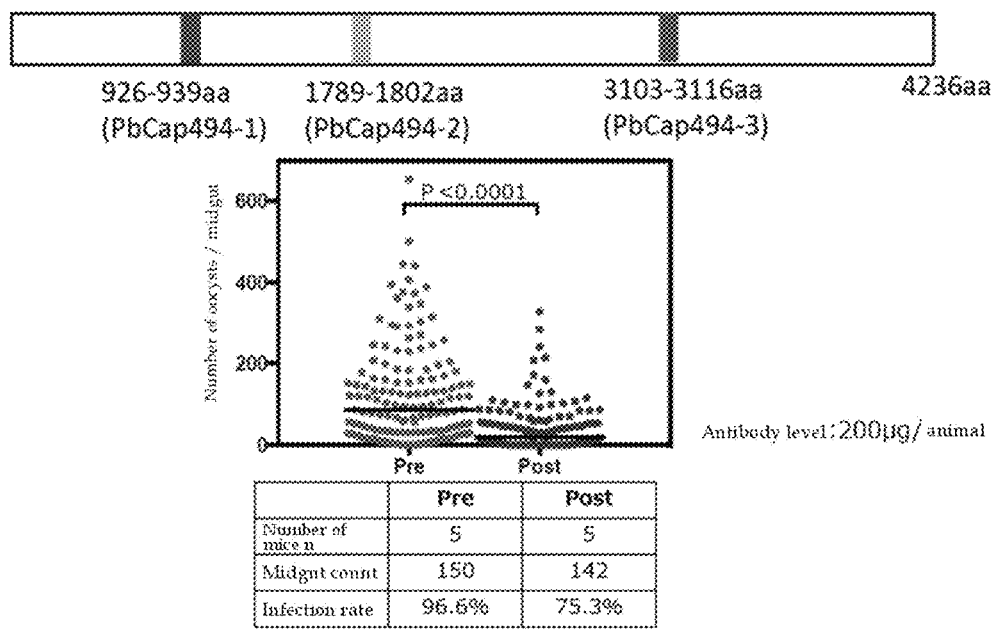

[Figure 4]
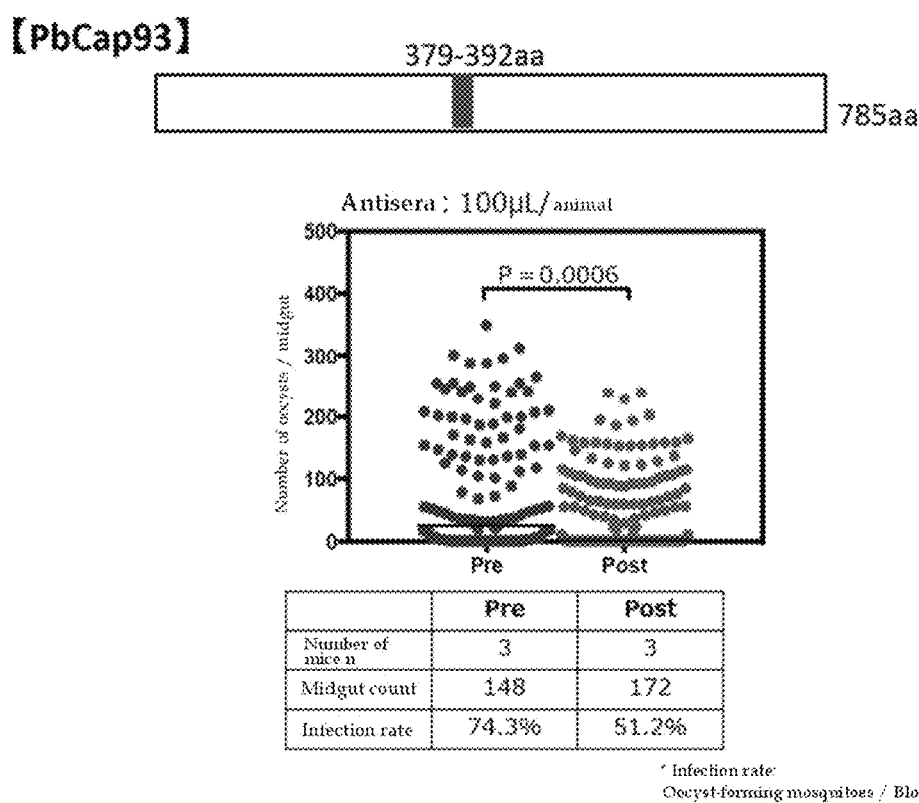

[Figure 5]
【control】
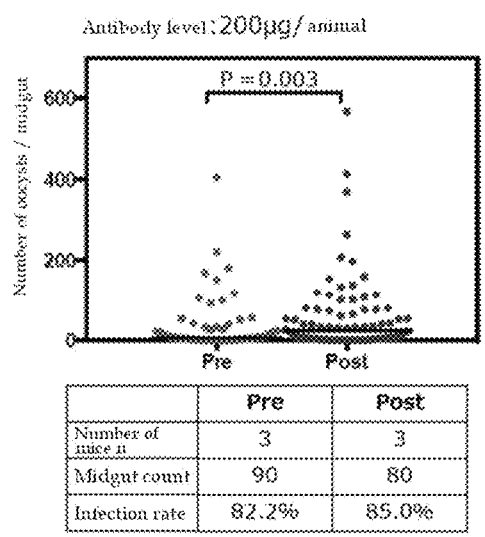

[Figure 6]
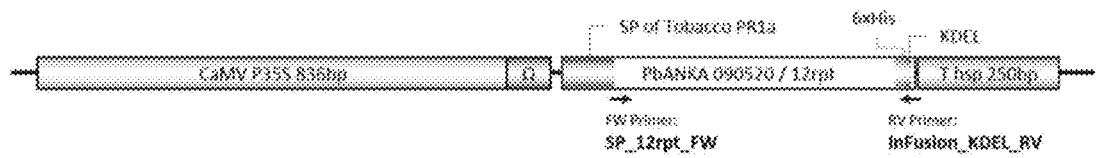
[Figure 7]
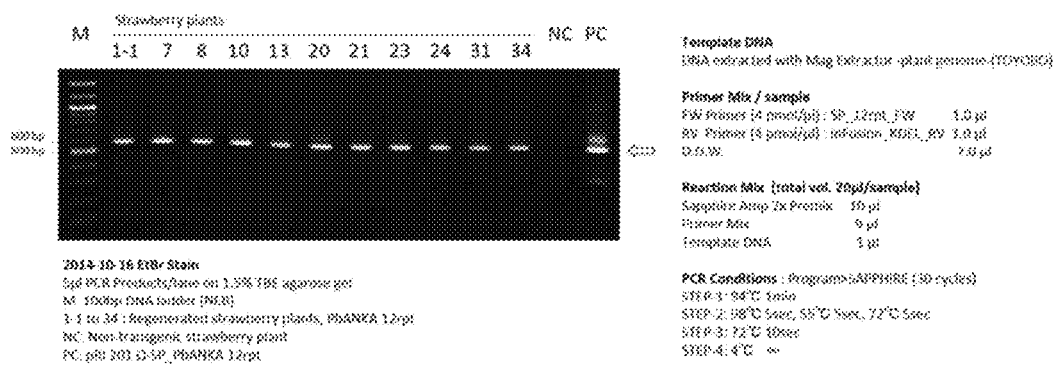
[Figure 8]
Immunological Evaluation of an Oral Vaccine Using Transformed Strawberry
: Antibody reactivity upon boosting strawberry to injected immunized mice.
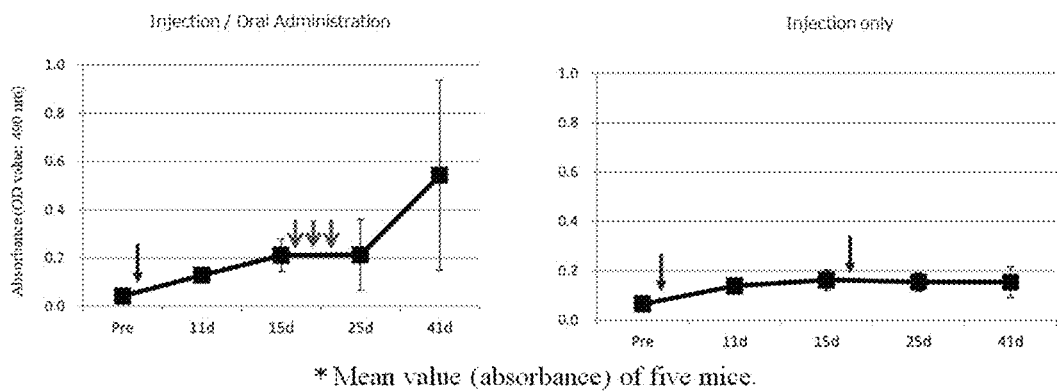
*Mean value (absorbance) of five mice.
↓: Injections
⇩: Oral administration

MALARIA TRANSMISSION BLOCKING VACCINE

RELATED APPLICATION

This application is a national stage filing under 35 U.S.C. § 371 of International Patent Application Serial No. PCT/JP2017/031784, filed Sep. 4, 2017, the contents of which are incorporated herein by reference in its entirety.

TECHNICAL FIELD

The present invention relates to a malaria transmission-blocking vaccine for preventing the transmission of malaria, in particular said vaccine for oral use.

BACKGROUND ART

Malaria is an infectious disease that is widely distributed from tropical to subtropical, and is caused primarily by infection with *Plasmodium malariae* (*Plasmodium falciparum*), which is mediated by mosquitoes (*Anopheles gambiae*). *Plasmodium malariae* have a life cycle in which they sexually reproduce in the digestive tract of *Anopheles* mosquitoes and develop into the next infectious type (Non-Patent Document 1). Prevention of the transmission of malaria by inhibiting the development of parasites in *Anopheles* mosquitoes has been considered as a transmission-blocking vaccine, and antigens expressed in gametes and orchinates in the development stage of malaria parasites have been investigated as an active ingredient of such transmission-blocking vaccines (Patent Document 1), but they have not been sufficient yet.

CITATION LIST

Patent Documents

[Patent Document 1] JP-A-2003-277292

Non-Patent Documents

[Non-Patent Document 1] Crompton P. D. et al. "Advances and challenges in malaria vaccine development" (2010) J Clin Invest. 120(12):4168-78.

SUMMARY OF INVENTION

Problems to be Solved by Invention

Although the use of orchinates and gametes in the life cycle of malaria parasites as vaccine targets has been investigated previously, the use of oocysts formed in the midgut of *Anopheles* mosquitoes as vaccine targets has not been studied. Therefore, the present inventors thought that if this oocyst is used as a vaccine target, a completely new vaccine targeting a new stage of development of malarial parasites could be developed.

Namely, the oocysts are present for a relatively long period of time in the body of *Anopheles* mosquitoes, the oocyst stage is presumed to be the weakest stage because the number of protozoa is the least in the early stage of oocyst formation, and unlike the antigenic mutation of the sporozoite protozoa by mitogenesis, the oocysts are unlikely to be mutated. Therefore, the inventors of the present invention considered that a transmission-blocking vaccine targeting such a stage of oocyst development has an extremely high potential and conducted research.

In addition, although a transmission-blocking vaccine for oral administration has been proposed (Patent Document 1), no transmission blocking activity by oral administration has been confirmed. Since it is necessary to immunize not only humans but also a wide variety of animals involved in the infection cycle of malaria in order to make a transmission-blocking vaccine effective, the realization of an oral vaccine is a very effective form that can be immunized by feeding a wide variety of animals including wild animals.

It is therefore an object of the present invention to provide an entirely novel transmission-blocking vaccine using an immunogenic protein specifically expressed in the oocyst stage of the malaria parasite, which has not been investigated so far, and a transmission-blocking vaccine for oral administration capable of immunizing various animals involved in the malaria infectious cycle with such a vaccine.

Means for Solving Problems

In order to solve the above-mentioned problems, the present inventors found that a protein specifically expressed in malaria parasites during the oocyst stage effectively functions as a transmission-blocking vaccine for inhibiting the development of oocysts, and further produced a transformed plant incorporating DNA encoding such a protein or a part thereof so as to be expressible, and confirmed the vaccine effect as a transmission-blocking vaccine for oral administration using the same, and as a result of further advancing research, the present invention was completed.

Namely, the present invention relates to the following.

[1] A malaria transmission-blocking vaccine, comprising an immunogenic protein derived from malaria parasite specifically expressed in the oocyst stage of the malaria parasite, wherein the immunogenic protein derived from the malaria parasite is (a1) a protein consisting of the amino acid sequence set forth in SEQ ID NO: 1;

(b1) a protein consisting of an amino acid sequence having 90% or more identity to the amino acid sequence set forth in SEQ ID NO: 1, and having immunogenicity;

(a2) a protein consisting of the amino acid sequence set forth in SEQ ID NO: 2; or (b2) a protein consisting of an amino acid sequence having 90% or more identity to the amino acid sequence set forth in SEQ ID NO: 2, and having immunogenicity.

[2] A malaria transmission-blocking vaccine, comprising a polypeptide that is a peptide fragment of an immunogenic protein derived from malaria parasite that is specifically expressed in the oocyst stage of the malaria parasite, wherein the polypeptide is (a1) a polypeptide consisting of the amino acid sequence set forth in SEQ ID NO: 3;

(b1) a polypeptide consisting of an amino acid sequence having 90% or more identity to the amino acid sequence set forth in SEQ ID NO: 3, and having immunogenicity;

(a2) a polypeptide consisting of the amino acid sequence set forth in SEQ ID NO: 4, 5 or 6; or (b2) a polypeptide consisting of an amino acid sequence having 90% or more identity to the amino acid sequence set forth in SEQ ID NO: 4, 5 or 6 and having immunogenicity.

[3] The malaria transmission-blocking vaccine according to the above [1] or [2], which is for oral use.

[4] A malaria transmission-blocking vaccine for oral use, comprising an immunogenic protein derived from malaria parasite specifically expressed in the oocyst stage of the malaria parasite or a peptide fragment thereof.

[5] The malaria transmission-blocking vaccine according to any one of the above [1] to [4], comprising a transformant expressing an immunogenic protein derived from the malaria parasite or a peptide fragment thereof.

[6] A malaria transmission-blocking vaccine according to any one of the above [1] to [4], comprising an edible tissue of a transformant expressing an immunogenic protein derived from the malaria parasite or a peptide fragment thereof.

[7] The malaria transmission-blocking vaccine according to the above [6], wherein the edible tissue can be eaten raw.

[8] The malaria transmission-blocking vaccine according to any one of the above [5] to [7], wherein the transformant is a transformed plant.

[9] The malaria transmission-blocking vaccine of the above [8], wherein the transformed plant is strawberry and the edible tissue is strawberry fruit.

[10] The malaria transmission-blocking vaccine according to any one of the above [5] to [9], wherein the transformant expresses DNA encoding a protein consisting of the amino acid sequence of SEQ ID NO: 1 or a peptide fragment thereof; or a protein consisting of the amino acid sequence of SEQ ID NO: 2 or a peptide fragment thereof.

[11] The malaria transmission-blocking vaccine according to the above [10], wherein the expressed DNA is
(a1) DNA consisting of the nucleotide sequence set forth in SEQ ID NO: 7 or 8;
(b1) DNA that hybridizes under stringent conditions to a DNA consisting of a nucleotide sequence complementary to the DNA consisting of the nucleotide sequence described in (a1), and that encodes a protein having immunogenicity;
(a2) DNA consisting of the nucleotide sequence set forth in SEQ ID NO: 9, 10, 11 or 12; or
(b2) DNA that hybridizes under stringent conditions to a DNA consisting of a nucleotide sequence complementary to the DNA consisting of the nucleotide sequence described in (a2), and that encodes an immunogenic peptide fragment.

[12] A transformant expressing an immunogenic protein derived from malaria parasite or a peptide fragment thereof, wherein DNA encoding a protein consisting of the amino acid sequence set forth in SEQ ID NO: 1 or a peptide fragment thereof; or a protein consisting of the amino acid sequence set forth in SEQ ID NO: 2 or a peptide fragment thereof; is introduced to the transformant so as to be expressible.

[13] The transformant according to the above [12], wherein the introduced DNA so as to be expressible is
(a1) DNA consisting of the nucleotide sequence set forth in SEQ ID NO: 7 or 8;
(b1) DNA that hybridizes under stringent conditions to a DNA consisting of a nucleotide sequence complementary to the DNA consisting of the nucleotide sequence described in (a1), and that encodes a protein having immunogenicity;
(a2) DNA consisting of the nucleotide sequence set forth in SEQ ID NO: 9, 10, 11 or 12; or
(b2) DNA that hybridizes under stringent conditions to a DNA consisting of a nucleotide sequence complementary to the DNA consisting of the nucleotide sequence described in (a2), and that encodes an immunogenic peptide fragment.

[14] A method of blocking the transmission of malaria, comprising administering the malaria transmission-blocking vaccine according to any one of the above [1] to [11] to a domestic or wild animal.

[15] The method according to the above [14], wherein the administration is oral administration.

Effects of Invention

As for a malaria transmission-blocking vaccine, it has been utilizing immunogenic proteins specifically expressed in gametes and orchinates. It has been found that an immunogenic protein derived from the malaria parasite specifically expressed in the oocyst stage of the malaria parasite or a part thereof is effective as a transmission-blocking vaccine in the present invention. In addition, transformed plants that expressably integrate DNA encoding such proteins or portions thereof are capable of immunizing a variety of animals involved in the infectious cycle as an oral vaccine, thus disrupting the infectious cycle of malaria.

BRIEF DESCRIPTION OF DRAWINGS

FIG. 1 shows the results of fluorescent antibody staining for anti-PbCap93-1 and anti-PbCap494-1 antibody against oocysts.

FIG. 2 shows the inhibition of oocyst formation by passive immunization using rabbit antibody (anti-PbCap494-1 antibody) obtained by immunization with polypeptide PbCap494-1.

FIG. 3 shows the inhibition of oocyst formation by passive immunization using mixed rabbit antibodies with anti-PbCap494-2,3 antibody and anti-PbCap494-1 antibody. Anti-PbCap494-2,3 antibody was obtained by immunization with combined peptide of two regions PbCap494-2 and PbCap494-3.

FIG. 4 shows inhibition of oocyst formation by passive immunization using rabbit antibodies obtained by immunization with polypeptides PbCap93-1.

FIG. 5 shows inhibition of oocyst formation by passive immunization using non-immunized rabbit antibodies.

FIG. 6 shows plant expression constructs incorporating DNAs encoding polypeptides PbCap93-1.

FIG. 7 is an electrophoretic diagram confirming the introduction of DNAs encoding polypeptides PbCap93-1 in transformed strawberry strains by genomic PCR.

FIG. 8 shows the increase in antibody titer following administration of an oral vaccine utilizing transformed strawberries.

EMBODIMENTS FOR CARRYING OUT INVENTION

In one embodiment of the present invention, the malaria transmission-blocking vaccine of the present invention comprises an immunogenic protein derived from the malaria parasite or a peptide fragment thereof which is specifically expressed in the oocyst stage of the malaria parasite. Here, as long as the peptide fragment has immunogenicity, there is no particular limitation on the type or number of amino acids constituting the peptide fragment, and for example, it includes an oligopeptide consisting of about 10 amino acids and a peptide consisting of 20 or more amino acids. In this specification, unless otherwise specified, a peptide consisting of two or more amino acids is referred to as a polypeptide.

In one embodiment, the immunogenic protein from the malaria parasite is a protein PbCap93 or protein PbCap494 from the malaria parasite (*Plasmodium berghei*), or an immunogenic protein consisting of various proteins from the malaria parasite corresponding thereto, or an amino acid sequence having 90% or more, preferably 95% or more identity to their amino acid sequence.

The immunogenic protein includes (1) a protein PbCap93 consisting of the amino acid sequence set forth in SEQ ID NO: 1, (2) a protein consisting of an amino acid sequence having 90% or more, preferably 95% or more identity to the amino acid sequence set forth in SEQ ID NO: 1 and having immunogenicity, (3) a protein PbCap494 consisting of the amino acid sequence set forth in SEQ ID NO: 2, and (4) a protein consisting of an amino acid sequence having 90% or more, preferably 95% or more identity to the amino acid sequence set forth in SEQ ID NO: 2 and having immunogenicity.

In one embodiment, the immunogenic polypeptides may be peptide fragments of protein PbCap93 or peptide fragments of protein PbCap494. Furthermore, peptide fragments of proteins derived from various malaria parasites corresponding to protein PbCap93 or protein PbCap494 may be used.

An immunogenic polypeptide of the present invention is: (a1) a polypeptide PbCap93-1 consisting of the amino acid sequence set forth in SEQ ID NO: 3; (a2) a polypeptide consisting of an amino acid sequence having 90% or more, preferably 95% or more identity to the amino acid sequence set forth in SEQ ID NO: 3, and having immunogenicity; (b1) a polypeptide PbCap494-1 consisting of the amino acid sequence set forth in SEQ ID NO: 4; (b2) a polypeptide consisting of an amino acid sequence having 90% or more, preferably 95% or more identity to the amino acid sequence set forth in SEQ ID NO: 4, and having immunogenicity; (c1) a polypeptide PbCap494-2 consisting of the amino acid sequence set forth in SEQ ID NO: 5; (c2) a polypeptide consisting of an amino acid sequence having 90% or more, preferably 95% or more identity to the amino acid sequence set forth in SEQ ID NO: 5, and having immunogenicity; (d1) a polypeptide PbCap494-3 consisting of the amino acid sequence set forth in SEQ ID NO: 6; (d2) a polypeptide consisting of 90 Preferably, a polypeptide comprising an amino acid sequence having 95% or more identity, and having immunogenicity is included.

In one embodiment of the present invention, there is a malaria transmission-blocking vaccine comprising an immunogenic protein comprising at least one of the polypeptides of (a1)-(d2) above. An immunogenic protein comprising at least one of the polypeptides (a1) to (d2) includes a protein PbCap93 comprising the amino acid sequence set forth in SEQ ID NO: 1; a protein PbCap494 comprising the amino acid sequence set forth in SEQ ID NO: 2; and a protein comprising an amino acid sequence having 90% or more and preferably 95% or more identity with the amino acid sequence mentioned above, and having immunogenicity.

Further, the immunogenic polypeptide of the present invention includes a polypeptide consisting of the above (a1) to (d2) as a building block and such building blocks are repeated regularly, for example, (a1)-(a2)-(a1)-(a2)- . . . -(a1)-(a2), (a1)-(b1)-(c1)-(d1)- . . . -(c1)-(d1) and so on, or, such building blocks are repeated irregularly, for example, (a1)-(b2)-(b1)-(b2)- . . . -(a2)-(a2), or (a2)-(b1)-(c1)-(b2)- . . . -(d2)-(b2) and so on.

When the building block is repeatedly included, the number of repetitions is not particularly limited.

The vaccine of the present invention may be for oral administration.

The present invention may also, in one embodiment, be a malaria transmission-blocking vaccine for oral administration comprising an immunogenic polypeptide derived from malaria parasites specifically expressed in the oocyst stage of the malaria parasite.

In the present invention, the "malaria transmission-blocking vaccine" may be any vaccine that prevents the transmission of malaria. For example, it may be a vaccine containing an antigen which is expressed in the malaria parasite at a stage of development in the body of a mosquito vector of the malaria parasite.

The malaria to be prevented from transmission by the vaccine of the present invention is not particularly limited as long as it is mediated by the malaria parasite which specifically expresses the immunogenic protein in the oocyst stage. For example, not only falciparum malaria (*Plasmodium falciparum*), vivax malaria (*Plasmodium vivax*), quartan malaria (*Plasmodium malariae*), simian malaria (*Plasmodium knowlesi*), rodent malaria (*Plasmodium berghei*), etc. can be prevented from malaria transmission mediated by known malaria parasites. In particular, transmission of malaria mediated by malaria parasites expressing a protein corresponding to protein PbCap93 or protein PbCap494 of rodent malaria parasite (*Plasmodium berghei*) can be suitably prevented.

The malaria parasites have a predetermined stage of development in the body of *Anopheles* mosquitoes. In other words, malaria parasites invade *Anopheles* mosquitoes by blood-sucking action, and are transformed into male and female reproductive bodies in the digestive tract of the mosquitoes, becoming zygotes in both sexes, and differentiating from orchinates into oocysts.

The polypeptide may be synthesized according to conventional methods, and may be obtained, for example, by culturing transformed host cells, expressing the target DNA incorporated in the expression vector, and purifying the protein. For example, host cells are destroyed by ultrasonic treatment, homogenizer treatment, high pressure compaction treatment, and the like to obtain an extract, and the extract can be separated and purified by combining methods such as solvent extraction, salting-out, desalting, organic solvent precipitation, ultrafiltration, ion-exchange, hydrophobic interaction, HPLC, gel filtration and affinity chromatography, electrophoresis, isoelectric focusing, and the like.

The host cells used for transformation can be, for example, microorganisms of the genera *Escherichia* and *Bacillus* as prokaryotes, yeasts of the genera *Saccharomyces, Schizosaccharomyces* and *Pichia* as eukaryotes, mammalian cells such as Chinese hamster ovary (CHO) cells of human fetal kidney cells, baculovirus-sensitive insect cells and insect bodies.

When the vaccine of the present invention is to be used orally, for example, it may be prepared by the usual method of the formulation according to the method described in the "General Rules for Formulations of the Japanese Pharmacopoeia, 15th revision" and suitable for oral use. The dosage form can include capsules, granules, pills, powders, tablets, and the like, and various additives, for example, excipients, binders, disintegrants, coating agents, and the like, may be formulated depending on the dosage form for oral use. Oral dietary modifiers are also not limited to only artificially formulated compositions, but include, for example, food ingredients such as vegetables and fruits such as leaves, roots and fruits, food ingredients, processed end products such as foods and beverages, as well as various compositions used for foods, and represent concepts that encompass anything that is about to be eaten or fed.

The vaccines of the present invention may contain transformants that express immunogenic polypeptides derived from the malaria parasite. The transformant is not particularly limited as long as it has no problem in feeding and the polypeptide is expressed by transformation and can be orally immunized. For example, transformants of microorganisms conventionally used in foods such as natto bacteria, lactic acid bacteria, acetic acid bacteria, yeast and basidiomycetes, and transformed animals highly expressing the aforementioned polypeptides may be used, but transformed plants such as rice, wheat, barley, maize, strawberry, tomato, potato, lettuce, soybean and azuki are preferable because it is to be used especially orally and possible to avoid the risk of contamination of pathogens (viruses, fungi, bacteria, parasites, and the like) infectious to animals.

Preferably, the transformant has an edible tissue. Such edible tissues include, for example, basidiomycete fruits (mushrooms), plant fruits (e.g., strawberries, tomatoes), roots (radishes, potatoes), leaves (cabbage, lettuce), seeds (rice, barley, wheat, corn, and other cereals, and soybeans, azuki, and the like). Among them, an edible tissue to be eaten raw is preferable because immunogenicity is not deactivated by cooking such as heating and such tissue is easy to eat or feed.

Methods of making transformants are not particularly limited and can be produced by generally well known methods. For example, transformation methods suitable for a variety of subjects can be used, such as methods utilizing calcium-based competencies (mainly bacteria), vectors such as phage and plasmids (mainly bacteria), protoplast-PEG methods (mainly filamentous fungi), lithium methods (mainly yeast), electroporation methods, particle gun methods, *Agrobacterium* methods (plants).

The transformants which can be used in the present vaccines are introduced so that DNA encoding an immunogenic protein derived from malaria parasites which is specifically expressed in the oocyst stage of malaria parasites or a peptide fragment thereof, in particular, DNA encoding a protein PbCap93 or a peptide fragment thereof, DNA encoding a protein PbCap494 or a peptide fragment thereof, or the like can be expressed.

In one embodiment, the present invention provides that the expressed DNA is,
(a1) DNA consisting of the base sequence set forth in SEQ ID NO: 7 (DNA encoding protein PbCap93); or DNA consisting of the base sequence set forth in SEQ ID NO: 8 (DNA encoding protein PbCap494);
(b1) DNA that hybridizes under stringent conditions to a DNA consisting of a nucleotide sequence complementary to the DNA consisting of the nucleotide sequence described in (a1), and that encodes a protein having immunogenicity;
(a2) DNA consisting of the base sequence set forth in SEQ ID NO: 9 (DNA encoding a polypeptide PbCap93-1), DNA consisting of the base sequence set forth in SEQ ID NO: 10 (DNA encoding a polypeptide PbCap494-1), DNA consisting of the base sequence set forth in SEQ ID NO: 11 (DNA encoding a polypeptide PbCap494-2), or DNA consisting of the base sequence set forth in SEQ ID NO: 12 (DNA encoding a polypeptide PbCap494-3); or
(b2) DNA that hybridizes under stringent conditions to a DNA consisting of a nucleotide sequence complementary to the DNA consisting of the nucleotide sequence described in (a2), and that encodes a peptide having immunogenicity.

The present invention relates, in one aspect, to transformants expressing immunogenic polypeptides derived from malaria parasites.

The transformant of the present invention is a transformant that can be used in the vaccines of the present invention described above, and, for example, a protein PbCap93 having the amino acid sequence set forth in SEQ ID NO: 1 or a peptide fragment thereof; or a DNA encoding a protein PbCap494 having the amino acid sequence set forth in SEQ ID NO: 2 or a peptide fragment thereof is introduced so as to be expressible.

In one embodiment of the invention, the transformants are those that
(a1) DNA consisting of the nucleotide sequence set forth in SEQ ID NO: 7 or 8;
(b1) DNA encoding a protein that hybridizes under stringent conditions to a DNA consisting of a nucleotide sequence complementary to the DNA consisting of the nucleotide sequence described in
(a1), and has immunogenicity;
(a2) DNA consisting of the nucleotide sequence set forth in SEQ ID NO: 9, 10, 11 or 12; or
(b2) DNA that hybridizes under stringent conditions with a DNA consisting of a nucleotide sequence complementary to the DNA consisting of the nucleotide sequence described in (a2), and that encodes an immunogenic peptide fragment; is introduced so as to be expressible.

The term "stringent conditions" as used herein refers to conditions under which specific hybrids are formed and non-specific hybrids are not formed. Such conditions are understood by those skilled in the art and include, for example, conditions in which nucleic acids having a high degree of homology, such as 99.5% or more, hybridize to each other, but DNA having a lower degree of homology does not hybridize to each other.

The present invention relates, in one aspect, to a method of preventing the transmission of malaria, wherein the method comprises, for example, administering to a domestic or wild animal a malaria transmission inhibiting vaccine of the present invention.

Administration to domestic or wild animals in the present invention may be parenteral, but oral administration is preferred. Parenteral administration includes administration by injection, transdermal, transmucosal, nasal or pulmonary administration. Oral administration may be accomplished, for example, by feeding the edible tissue of the transformants to domestic or wild animals. Feeding includes not only feeding the livestock in the breeding environment, but also sprinkling the edible tissue into the wild environment so that the wild animal can feed.

As used herein, immunogenicity refers to the property of inducing an immune response. Such properties include, for example, antigenicity that triggers a biological reaction that produces antibodies by immunization, and properties that modulate immune-related substances such as cytokines and inflammatory factors.

The vaccine of the present invention may contain an adjuvant, for example, an aluminum hydroxide gel, an aluminum phosphate gel, a mixture of a vegetable or mineral fat and a surfactant, or the like. The amount of the adjuvant is not particularly limited as long as it can be immunostimulated in accordance with the characteristics of each adjuvant.

The vaccine of the present invention can be used as a normal vaccine, for example, it can be administered multiple times to obtain a booster effect. It can also be used for boosters after administration of other vaccines. For example, a booster effect can be obtained by orally administering to an individual who has previously been administered a vaccine of the same kind or different kind as the vaccine of the present invention. Pre-administered vaccines are not particularly limited in dosage form and may be administered by injection, transdermal, transmucosal, nasal or pulmonary administration, or orally.

In the following, the method according to the present invention will be explained in more detail on the basis of examples and test examples, but the present invention is not limited thereto.

EXAMPLES (a) Selection of Candidate Genes for Expressed Proteins in the Oocyst Stage Using 'Identify Genes based on P. b. life cycle MassSpec.Evidence(hypertext transfer protocol plasmod-b.org/a/showQuestion.d
o?questionFullName=GeneQuestions.GenesByProteomicsProfile)' of Plasmo DB (hypertext transfer protocol plasmod-b.org/plasmo/), 14 genes with transmembrane regions were selected out of 65 genes expressed only in the oocyst stage, and 5 genes including PBCAP93 and PBCAP494 which are novel proteins were selected as candidates. The peptides described in Table 1 were conjugated to KLH using the maleimide method and immunized to Japanese white rabbits each. Antibody production was performed using the antibody production services of eurofins operon Corporation.

TABLE 1

Candidate Genes and Tested Amino Acid Regions

| Peptide name | Gene ID | Amino acid region |
|---|---|---|
| PbCap93-1 | PBANKA_090520 | 379-392aa |
| PbCap494-1 | PBANKA_102510 | 926-939aa |
| PbCap494-2 | PBANKA_102510 | 1789-1802aa |
| PbCap494-3 | PBANKA_102510 | 3103-3116aa |

(b) *E. coli* Expression of PbCap93-1

Constructs in which DNAs encoding the respective amino acid regions listed in Table 1 were repeated 12 times were produced and expressed in the pCold III vector system (TAKARA).

The PCR-amplified fragments obtained using the primers described below were each treated with a plasmid vector digested with restriction enzymes (Nde I/Pst I) and then introduced into a plasmid, and the plasmid was used to obtain an *E. coli* BL21 (Agilent Technologies Cat. 230245) transformed strain for expression.

```
FW Primer:
                              (SEQ ID NO: 13)
5'-GAATTCCATATGATGATTTCCCATAACCACAACGACCAT-3'

RV Primer:
                              (SEQ ID NO: 14)
5'-GAACTGCAGTCAAAGTTCATCCTTATGATGATGGTGGTG-3'
```

Subsequently, the transformed *E. coli* strain in which the plasmid was inserted was inoculated into 10 ml of LB medium containing 100 μg/ml of ampicillin, shaken and cultured at 30° C. overnight. *E. coli* cells containing plasmids were inoculated into LB medium containing 100 μg/ml of ampicillin (200 ml×2), shaken and cultured at 37° C., cooled to 15° C. immediately when the OD 600 of the culture medium reached 0.4 to 0.5, and left for 30 minutes. IPTG was added to a final concentration of 1.0 mM and the mixture was shaken at 15° C. overnight.

(c) Purification of Expressed Proteins

*Escherichia coli* (400 ml) after induction of IPTG expression is harvested, B/W Buffer is added, and crushed by supersonic crushing. After that, the mixture was centrifuged (9800×g, 10 min), the supernatant was mixed into 4 ml (Bed Volume) of Ni-NTA Agarose (QIAGEN Cat. 1018240) and adsorbed overnight at 4° C. using a shaker. After overnight adsorption, the supernatant was centrifuged (2000×g, 2 minutes) and discarded, and the Ni-NTA Agarose was centrifuged and washed with B/W Buffer (2000×g, 2 minutes×2 times). POLY-PREP® Chromatography Columns (BIO RAD Cat. 731-1550) was filled with Ni-NTA Agarose and washed with B/W Buffer (4×10 ml). The attached Elution Buffer1 ~5 was sequentially passed through a POLY-PREP® Chromatography Columns in 5 ml portions, and the fractions were collected.

(d) ELISA of Expressed Proteins to Determine Titers

Purified expressed protein dissolved in PBS was added to 96 well plates and immobilized overnight at 4° C. After blocking, 100 μl of anti-PbCap93-1 antibodies were added and reacted at 4° C. for 2 hours. After washing with PBS, peroxidase conjugated anti-rabbit IgG was added, reacted at 4° C. for 2 hours, and after washing and colorizing, the absorbance was measured to confirm the antibody titer of the antibody produced in (a).

(e) Confirmation of the Peptide Antibody Recognition of the Proteins Expressed in the Oocyst Stage The midgut of *A. gambiae* (Keele strain) 15 days after *P. berghei* infection by blood-sucking was smeared and air-dried on a glass slide and then fixed with methanol. After air-drying, the smeared midgut was surrounded by Liquid Blocker (Daido Sangyo, Japan), and one drop of Image-iT (trademark) FX Signal Enhancer (Invitrogen USA) was dropped, and left to stand at 37° C. for 30 minutes. After washing with PBS, rabbit sera containing anti-PbCap93-1 and anti-PbCap494-1 antibody as the primary antibody were reacted at 4° C. for 2 hours, washed 2 or 3 times with PBS, and ALEXA FLUOR™ 488 anti-rabbit IgG (Molecular Probes, USA) (1:800-fold diluted) as the secondary antibody was reacted at 4° C. for 1 hour, and washed 2 or 3 times with PBS. In addition, anti-PbCap380 rabbit sera (1:1000-fold dilution) as a primary antibody was reacted for 1 hour at 4 degrees, washed 2 or 3 times with PBS, and ALEXA FLUOR™ 568_anti-rabbit IgG (Molecular Probes, USA) (1:800-fold dilution) as a secondary antibody was reacted for 1 hour at 4° C. and washed 2 or 3 times with PBS. Nuclei were stained by adding Hoechest 33258 (Polysciences, USA) to secondary antibodies at a final concentration of 5 μg/ml. One drop of FLUOROMOUNT/PLUS™ SAMPLE (Diagnostic Bio System, USA) was dropped on a glass slide, covered with a coverslip, and observed under a fluorescent microscope, and the results are shown in FIG. 2. It was revealed that these antibodies recognize oocysts and that PbCap93 and PbCap494 are located on the outer side of the oocyst walls.

(f) Inhibition of Oocyst Formation by Passive Immunization PbCap494-1~3

*Plasmodium berghei* (1×10⁶) was administrated intravenously(tail vein) to Balb/c mice. The mosquitoes (*Anopheles stephensi*) used were divided into two boxes before (pre) and after (Post) serum administration, and 100 mosquitoes (including both sexes) were prepared for each box. When the erythrocyte infestation (parasitemia) rate (infected erythrocytes/total erythrocytes) was around 10%, mosquitoes were fed for 10 minutes (pre-infected mosquitoes). Then, anti-PbCap494 rabbit antibodies (anti-PbCap494-1 antibody and anti-PbCap494-2,3 antibody) by immunization with the PbCap494-1 peptide and the peptide combining the two regions of PbCap494-2 and p3 were administered in the tail vein to the malaria-infected mice. Mosquitoes were fed for 10 minutes (Post infected mosquitoes) 5 minutes after administration in the tail veins. Pre-infected mosquitoes and Post infected mosquitoes were dissected (30 or more animals) 15 days after the infection by blood-sucking, and the numbers of oocysts formed in the middle intestine of mosquitoes were counted and compared. Results of administration in the tail vein of 10 µg/mouse and 200 µg/mouse of PbCap494-1 antibodies are shown in FIG. 2. The number of oocysts was significantly decreased at both 10 µg and 200 µg doses, and the number of oocysts tended to decrease more at higher antibody levels. FIG. 3 shows the results of administering 200 mice per 100 µg each of anti-PbCap494-1 antibody and anti-PbCap494-2,3 antibody. The number of oocysts was significantly decreased in the treated group.

PbCap93-1

*Plasmodium berghei* ($1 \times 10^7$) was administered intraperitoneally(tail vein) to Balb/c mice. The mosquitoes (*Anopheles stephensi*) used were divided into two boxes before (pre) and after (Post) serum administration, and 100 mosquitoes (including both sexes) were prepared for each box. When the rate of erythrocyte infestation (parasitemia) rate (infected erythrocytes/total erythrocytes) of the above mice was around 10%, mosquitoes were fed for 10 minutes (pre-infected mosquitoes). Subsequently, anti-PbCap93-1 rabbit sera were administered in the tail vein to malaria-infected mice (100 µl). Mosquitoes are fed for 10 minutes (Post infected mosquitoes) 5 minutes after administration in the tail veins. Seven days after feeding, preinfected mosquitoes and Post infected mosquitoes were dissected (30 or more) and the numbers of oocysts formed in the middle intestine of mosquitoes were counted and compared. The results are shown in FIG. 4. The number of oocysts was significantly decreased in the treated group.

The results of the same administration of the control rabbit antibody are shown in FIG. 5. No treatment-related decrease in the number of oocysts was observed.

(g) Generation of Antigen-Expressing Strawberries Preparation of Vectors for Plant Expression A construct for plant expression for PbCap93-1 is shown in FIG. 6. The abbreviations in FIG. 6 are: CaMV P35S 836 bp: transcription promoting factor, Ω:TMV omega sequence, pRI 201 AN DNA(TAKARA) AN sequence substituted with Ω sequence, SP of Tobacco PR1: tobacco PR1 signal peptide sequence; Pb ANKA 090520/12rpt:Pbcap93 epitope sequence; Thsp 250 bp: *Arabidopsis* HSP gene-derived terminator sequence; His tag: histidine tag; KDEL: ER retention signal; FW Primer: forward primer; RV Primer: reverse primer. The above-mentioned pRI 201 AN DNA was commercialized by TAKARA in response to the provision of technology and samples from the National University Institute of Advanced Science and Technology, Nara University.

Plasmid Construction Methods

Using IN-FUSION® HD PCR Cloning Kit(TAKARA), Genes ware amplified by PCR with the primers described below, introduced into vectors linearized with Nde I and Sac I digestion, and the HB101 was transformed, and plasmids were recovered.

```
FW Primer:
                                   (SEQ ID NO: 15)
ttctacaactacacatATGGGATTCGTGCTTTTCTCTC RV Primer:
                                   (SEQ ID NO: 16)
cttcatcttcataagagctcTCAAAGTTCATCCTTATG
```

The lower case portion of the primer is a base sequence derived from a vector.

Transformation of Strawberry

Transformation mediated by *Agrobacterium* was carried out using the *Agrobacterium* strain into which above-mentioned plasmid was introduced.

Genomic PCR was performed using the specific FW Primer (forward primer) and RV Primer (reverse primer) set at both ends of the gene described below. The extraction of genomic DNAs was carried out according to a protocol using nucleic acid extraction kits MAGEXTRACTOR™-Plant Genome-(TOYOBO) and nucleic acid purification systems MAGEXTRACTOR™MFX-6100 TOYOBO). PCR products were detected by electrophoresis on a 1.5% TBE agarose gel, FIG. 7.

```
FW Primer:
                                   (SEQ ID NO: 17)
CTCTCACTCTTGCAGGGCTATTTCCCATAACCAC RV Primer:
                                   (SEQ ID NO: 18)
cttcatcttcataagagctcTCAAAGTTCATCCTTATG
```

The lower case portion of the primer is a base sequence derived from a vector.

(f) Immunological Evaluation of Oral Vaccines Using Transformed Strawberries

10 μg of PbCap93 were mixed with adjuvant (TITER MAX® Gold Funakoshi) (antigens:adjuvant=1:1), and Balb/c mice were immunized with 10 μg/100 μl/animal of the mixture by intramuscular injection. These mice were boosted by oral administration (approximately 0.1-0.15 g/dose of lyophilized transformed strawberry powder) on Days 2, 16, 20, and 24 after the primary immunization. Similarly, booster immunizations were performed by intramuscular injection on Days 2 and 28 after the primary immunization. On Days pre-administration, 11, 15, 25, and 41, mice were bled and the titers of the obtained sera against PbCap93-1 were determined by ELISA. In mice boosted with transformed strawberries, an increase in antibody titer was observed after Day 25. The results are shown in FIG. 8.

The sequence numbers and sequences described herein are shown in Table 2.

TABLE 2

| SEQ ID NO. and Sequences | |
|---|---|
| SEQ ID NO. | Sequence |
| SEQ ID NO: 1 | Full-length amino acid sequence of PbCap93 |
| SEQ ID NO: 2 | Full-length amino acid sequence of PbCap494 |
| SEQ ID NO: 3 | Amino acid sequence of PbCap93-1 |
| SEQ ID NO: 4 | Amino acid sequence of PbCap494-1 |
| SEQ ID NO: 5 | Amino acid sequence of PbCap494-2 |
| SEQ ID NO: 6 | Amino acid sequence of PbCap494-3 |
| SEQ ID NO: 7 | Full-length DNA sequence of PbCap93 |
| SEQ ID NO: 8 | Full-length DNA sequence of PbCap494 |
| SEQ ID NO: 9 | DNA sequence of PbCap93-1 |
| SEQ ID NO: 10 | DNA sequence of PbCap494-1 |
| SEQ ID NO: 11 | DNA sequence of PbCap494-2 |
| SEQ ID NO: 12 | DNA sequence of PbCap494-3 |
| SEQ ID NO: 13 | FW primer for PbCap93-1 transformed *E. coli* |
| SEQ ID NO: 14 | RV primer for PbCap93-1 transformed *E. coli* |
| SEQ ID NO: 15 | FW primer for PbCap93-1 plasmid |
| SEQ ID NO: 16 | RV primer for PbCap93-1 plasmid |
| SEQ ID NO: 17 | FW primer for PbCap93-1 transformed strawberry |
| SEQ ID NO: 18 | RV primer for PbCap93-1 transformed strawberry |

The invention claimed is:

1. A method of blocking the transmission of malaria comprising administering a malaria transmission-blocking vaccine to a domestic or wild animal,
wherein the malaria transmission-blocking vaccine comprises an immunogenic protein of a malaria parasite specifically expressed in the oocyst stage of the malaria parasite or a peptide fragment of the immunogenic protein, wherein the immunogenic protein is:
an isolated protein consisting of the amino acid sequence of SEQ ID NO: 1; or
an isolated protein consisting of the amino acid sequence of SEQ ID NO: 2; and
wherein the peptide fragment consists of the amino acid sequence of SEQ ID NO: 3 and/or one or more of SEQ ID NO: 4, SEQ ID NO: 5 and SEQ ID NO: 6.

2. The method according to claim 1, wherein the administration is oral administration.

3. The method according to claim 1, wherein the malaria transmission-blocking vaccine is a transformant plant expressing the immunogenic protein or the peptide fragment thereof, wherein the transformant plant is a strawberry plant.

4. The method according to claim 1, wherein the malaria transmission-blocking vaccine is an edible tissue of a transformant plant expressing the immunogenic protein or the peptide fragment thereof, wherein the edible tissue is strawberry fruit.

5. The method according to claim 3, wherein the transformant expresses a DNA encoding the protein consisting of the amino acid sequence of SEQ ID NO: 1 or the peptide fragment thereof; or the protein consisting of the amino acid sequence of SEQ ID NO: 2 or the peptide fragment thereof.

6. The method according to claim 5, wherein the expressed DNA is:
a DNA consisting of the nucleotide sequence set forth in SEQ ID NO: 7 or SEQ ID NO: 8; or
a DNA consisting of the nucleotide sequence set forth in SEQ ID NO: 9, SEQ ID NO: 10, SEQ ID NO: 11 or SEQ ID NO: 12.

\* \* \* \* \*

SEQUENCE LISTING

<160> NUMBER OF SEQ ID NOS: 18

<210> SEQ ID NO 1
<211> LENGTH: 785
<212> TYPE: PRT
<213> ORGANISM: Plasmodium berghei

<400> SEQUENCE: 1

```
Met Ala Asn Lys Asn Ile Asn Asn Gln Lys Ile Gln Lys Asp Glu Asn
1               5                   10                  15

Lys Lys Lys Asn Asp Glu Ser Glu Val Cys Asn Phe His Glu Val Asn
            20                  25                  30

Ile Ser Tyr Lys Lys Trp Val Lys Asp Lys Ile Gln Gln Gln Lys Ile
        35                  40                  45

Thr Leu Phe Asn Leu Lys Lys Tyr Asn Leu Ser Lys Lys Gln Lys Ser
    50                  55                  60

Ile Asn Ile Ile Ser Phe Ile Thr Ile Leu Ile Leu Asn Ile Ile
65                  70                  75                  80

Tyr Asn Arg Leu Ile Asp Ile Trp Tyr Asn Trp Asp Glu Ile Ile Glu
                85                  90                  95

Asn Phe Asp Glu Thr Lys Lys Cys Glu Asn Lys Asn Asp Tyr Asn Phe
            100                 105                 110

Asn Lys Tyr Ile Arg Gln Cys Ser Asn Phe Leu Lys Tyr Leu Met Lys
        115                 120                 125

Gly Ser Leu Asp Glu Asp Ile Tyr Asp Asn Asn Leu Glu Asn Asp
    130                 135                 140

Phe Ile Tyr Ile Lys Asn Ser Lys Ser Arg Asn Thr Ile Tyr Leu Lys
145                 150                 155                 160

Lys Ile Leu Gly Ser Glu Ile Ile Asp Asn Asn Tyr Ile Ser Val Tyr
                165                 170                 175

Leu Glu Asn Met Lys Tyr Leu Arg Asn Thr Ser Leu Asn Tyr Ser Val
            180                 185                 190

Asn Gln Arg Ser Leu Ser Thr Glu Trp Tyr Val Tyr Phe Arg Ser Phe
        195                 200                 205

Leu Lys Gln Ala Ile Thr Pro His Ser Leu Thr Lys Ala Ile Lys Ile
    210                 215                 220

Asp Lys Glu Tyr Ile Tyr Pro Trp Asp Val Ile Thr Gln Asp Asp Ala
225                 230                 235                 240

Glu Lys Ile Ile Glu Asn Ala Lys Phe Tyr Gly Phe Leu Phe Thr Trp
                245                 250                 255

Phe Lys Asn His Arg Lys Ala Gln Lys Val Asn Glu Ile Ile Leu Arg
            260                 265                 270

Lys Asp Met Pro Val Leu Ile Pro Lys Phe Ile Lys Ser Asp Phe Ser
        275                 280                 285

Gln Arg Leu Tyr Lys Asn Ser Lys Asn Asn Glu Pro Asn Phe Tyr Gly
    290                 295                 300

Ile His Tyr Thr Trp Leu Gly His Ala Thr Gly Leu Val Ile Val Asp
305                 310                 315                 320

Gly Leu Lys Ile Leu Val Asp Pro Val Phe Lys Ile Glu Leu Leu Ser
                325                 330                 335

Leu Lys Gly Ile Ala Arg Ser Leu Ile Asn Trp Val Asn Ile Lys Ile
            340                 345                 350

Met Gly Gly Leu Gly Glu Arg Ile Ser Lys Ser Pro Cys Asn Ile Ser
        355                 360                 365
```

```
Asn Leu Pro Asp Asp Leu His Ala Val Phe Ile Ser His Asn His Asn
370                 375                 380

Asp His Ile Met Glu Glu Asp Val Arg Ile Leu Cys Lys Leu Lys Lys
385                 390                 395                 400

Phe Lys Asp Val Met Trp Tyr Val Pro Glu Gly Thr Thr Ser Phe Phe
                405                 410                 415

Ile Gln Glu Gly Cys Lys Thr Asp Lys Ile Tyr Glu Leu Ser Trp Gly
                420                 425                 430

Asp Glu Arg Trp Val Ser Cys Trp Ile Asn Asn Lys Phe Thr Cys
            435                 440                 445

Lys Asp Gly Leu Trp Asn Asn Lys Lys Gly Asp Thr Asp Val Tyr Lys
450                 455                 460

Tyr Lys Ile Ile Tyr Ala Pro Ala Leu His Trp Ser Gly Arg Lys Gly
465                 470                 475                 480

Asp Leu Ser Asp Ile Asn Gln Ser Leu Trp Gly Ser Leu Ile Leu Lys
                485                 490                 495

Gly Pro Lys Ser Lys Phe Tyr Phe Ser Gly Asp Thr Ala Tyr Leu Lys
                500                 505                 510

Asp Asp Phe Glu Glu Phe Lys Lys Ile Gly Lys Leu His Gly Pro Phe
            515                 520                 525

Asp Phe Ala Ala Ile Ser Ile Gly Ala Tyr Glu Pro Asn Asn Ser Leu
530                 535                 540

Lys Tyr His His Ile His Pro Trp Glu Ser Val Lys Ile Trp Arg Asp
545                 550                 555                 560

Ile Arg Ala Glu Ile Ala Ile Gly Ile His Trp Gly Thr Phe Arg Leu
                565                 570                 575

Ser Ala Glu Glu Phe Leu Gln Pro Arg Asp Asp Leu Glu Ala Ala Leu
            580                 585                 590

Leu Gly Val Ser Leu Asn Thr Leu Arg Asn Tyr Asn Leu Thr Phe Glu
        595                 600                 605

Lys Lys Lys Met Glu Ile Leu Lys Lys Tyr Met Val Lys Asn Val Asn
            610                 615                 620

Ser Asn Asn Asp Ile Asp Asp Leu Glu Asp Leu Lys Glu Tyr Phe
625                 630                 635                 640

Tyr Pro Ala Ser Ser Thr Asp Tyr Asn Glu Tyr Thr Asp Ser Phe His
                645                 650                 655

Ser Ile Phe Ser Asn Asn Leu Ser Leu Phe Tyr Ser Asp Ile Asp Lys
                660                 665                 670

Asn Tyr Ile Lys His Met Tyr Gln Gln Lys Lys Leu Tyr Leu Ser Thr
            675                 680                 685

Tyr Asn Arg Tyr Lys Arg Ala Leu Ile Leu Lys Asn Ser Lys Lys Leu
        690                 695                 700

Pro Lys Ser Trp Lys Lys Leu Leu Leu Asn Leu Ser Ile Arg Phe Gln
705                 710                 715                 720

Thr Ile Pro Ile Gly Gly Ser Ile Glu Ile Lys Thr Lys Asp Asn Thr
                725                 730                 735

Ile Ser Met Thr Arg Ser Ser Glu Tyr Asn Ser Thr Ile Tyr Glu His
                740                 745                 750

Tyr Thr Phe Pro Lys Trp Tyr Lys Lys Glu Lys Glu Thr Leu
            755                 760                 765

Tyr Gln Tyr Asn Phe Pro His Glu Asp Leu Met Thr Phe Ser Ile Val
770                 775                 780

Asn
```

-continued

785

<210> SEQ ID NO 2
<211> LENGTH: 4236
<212> TYPE: PRT
<213> ORGANISM: Plasmodium berghei

<400> SEQUENCE: 2

Met Ser Thr Val Glu Asp Lys Met Asp Ile Asn Gln Asn Asn Val Asp
1               5                   10                  15

Leu Cys Lys Tyr Tyr Lys Asn Asn Thr Asn Asn Ser Asp Ala Leu
            20                  25                  30

Lys Tyr Asp Asp Tyr Phe Phe Arg Asp Leu Lys Lys Lys Asn Leu Asn
        35                  40                  45

Tyr Tyr Ile Lys Lys Asp Asn Tyr Cys Lys Ile Ile Leu Ser Asp Glu
50                  55                  60

Ser Asn Leu Gln Tyr Val Lys Trp Met Ile Asp Leu Met Asn Tyr Asn
65                  70                  75                  80

Lys Tyr Lys Lys Glu Ile Ser Leu Gln Val Leu Leu Asp Ile Gln Lys
                85                  90                  95

Ile Cys Asn Ser Ile Ser Leu Phe Phe Ile Lys Ile Tyr Ile His Ile
            100                 105                 110

Tyr Ile Tyr Leu Tyr Ala Leu Arg Arg Leu Tyr Leu Ser Val Phe Cys
        115                 120                 125

Val Ile Leu Lys Tyr Leu Ile Lys Lys Tyr Lys Cys Ile Ile Leu Asn
130                 135                 140

Lys Ile Gly Asp Ile Asn Lys Ile Asn Asn Leu Ser Asn Ile Lys Lys
145                 150                 155                 160

Val Lys Gly Ile Asp Lys Asn Ala Ser Asn Val Ile Leu Ile His Glu
                165                 170                 175

Ile Lys Cys Ser Ser Tyr Tyr Asp Trp Tyr Lys Ile Val Thr Asn Asp
            180                 185                 190

His Phe Glu Lys Asn Gly Lys Thr His Tyr Tyr Ser Ser Leu Ile Tyr
        195                 200                 205

Pro Lys Met Tyr Thr Gly Ile Leu Leu Val Ser Thr Asn Asn Tyr Tyr
210                 215                 220

Phe Val Leu Asn Lys Asn Val Asp Ile Lys Asn Asn Ser Lys Lys Leu
225                 230                 235                 240

Leu Met Leu Leu Met Asn Asn Met Val Asn Tyr Cys Gln Ile Asp Tyr
                245                 250                 255

Ile Glu Tyr Val Tyr Val Cys Asn Glu Ile Asn Asn Lys Lys Tyr Phe
            260                 265                 270

Asn Lys Cys Glu Lys Thr Asn Asn Lys Asn Ser Lys Ile Ile
        275                 280                 285

Val Cys Ile Ser Lys Thr Asn Arg Asn Phe Ile Ile Val Ala Tyr Asn
290                 295                 300

Ile Asn Lys Lys Asn Tyr Pro Cys Ile Lys Asn Ile Cys Gly Phe Ile
305                 310                 315                 320

Glu Lys Gln Arg Cys Tyr Asn Ala Pro Ser Tyr Tyr Lys Asn Met Cys
                325                 330                 335

Glu Lys Ile Tyr Thr Asn Asp Asn Asn Asn Asn Ile Ser Phe Ser
            340                 345                 350

His Ile Lys Tyr Tyr Leu Lys Leu Asp Thr Lys Ile Lys Lys Ser Lys
        355                 360                 365

-continued

```
Lys Ile Lys Asn Ser Leu Phe Asp Phe Arg Glu Asn Glu Asn Gln Ser
    370                 375                 380
Gly Tyr Ile Ile Tyr Lys Ile Pro Asn Asn Leu Cys Lys Lys Arg Glu
385                 390                 395                 400
Ile Ser Lys Met Tyr Asn Ile Lys Cys Asn Ile Leu Tyr Val Tyr Tyr
                405                 410                 415
Phe Phe Ala Thr Arg Gln Lys Asn Ile Val Ser Glu Ile Leu Tyr Tyr
            420                 425                 430
Ser Ser Cys Lys Asn Leu Thr Lys Gly Ile Tyr Tyr Glu Asp Phe His
        435                 440                 445
Leu Leu Phe Phe Leu Ile Lys Lys Leu Tyr Ile Phe Arg Lys Pro Leu
    450                 455                 460
Leu Val Ile Cys Leu Asn Asn Phe Glu Val Ile Asn Leu Phe Ile Ser
465                 470                 475                 480
Asp Ser Ile Asn Val Ile Tyr Cys Tyr Lys Ala Phe Ile Lys Lys Tyr
                485                 490                 495
Ile Leu Ser Lys Lys Tyr Asn Ile Ile Ser Lys Met Asp Val Met Thr
            500                 505                 510
Thr Tyr Tyr Tyr Ile His Phe Asn Leu Ser Lys Glu Arg Asn Ile Tyr
        515                 520                 525
His Thr Lys Ile Asn His Ile Leu Leu Asn Met Leu Asn Gly Arg Ile
    530                 535                 540
Cys Lys Lys Tyr Val Ile Lys Phe Cys Thr Glu Asp Cys Met Lys Ile
545                 550                 555                 560
Cys Ser Glu Tyr Tyr Ile Ile Ile Thr Leu Leu Lys Leu Tyr Ala Lys
                565                 570                 575
Tyr Phe Arg Thr Phe Ile Asn Ser Asn Phe Asp Phe Phe Gly Leu Leu
            580                 585                 590
Asn Cys Asn Ile Asn Phe Ile Asn Ile Ser Asn Asp Asp Asn Ile Asn
        595                 600                 605
Gly Ile Val Asn Asn Asn Arg Asp Thr Asn Asn Ser Ile Asn Phe His
    610                 615                 620
Arg Ser Thr Asn Tyr Ser Arg Ser Ile Leu Arg Lys Lys Arg Gly Lys
625                 630                 635                 640
Asn Arg His Leu His Asn Leu Gln Lys Tyr Ala Tyr Phe Ile Ile Phe
                645                 650                 655
Tyr Asn Ile Val Leu His Val Lys Asn Lys Pro Ile Lys Lys Ile Asn
            660                 665                 670
Ile Leu Phe Ser Glu Lys Asp Ser Leu Tyr Val Ile Lys Lys Leu Asn
        675                 680                 685
Asn Tyr Val Lys Lys Lys Lys Lys Phe Ile Leu Tyr Tyr Ile Tyr Asn
    690                 695                 700
Asn Ile Asp Ile Phe Phe Ile Arg Ala Asn Phe Lys Ser Asn Ile Arg
705                 710                 715                 720
Arg Asn Ile Phe Phe Lys Ile Ile Ile Lys Tyr Ile Lys Asn Val Glu
                725                 730                 735
Lys Leu Lys Arg Tyr Gly Glu Ile Cys Phe Phe Ser Lys Ile Ile Asn
            740                 745                 750
Leu Glu Phe Ile Gln Gln Lys Val Ile Asn Thr Phe Phe Ile Ser
        755                 760                 765
Lys Lys Cys Tyr Lys Phe Lys Tyr Tyr Asn Asn Leu Thr Lys Tyr Ile
    770                 775                 780
Tyr Ile Phe Phe Phe Leu Ile Ile Lys Cys Asn Glu Glu Leu Tyr Ser
```

```
              785                790                795                800
Lys Tyr Lys Ser Met Asn Ile Ile Arg Asn Glu Leu Lys Glu Lys
                805                810                815
Tyr Ile Glu Asn Ser Glu Lys Asn Phe Ser Asn Ile Phe Met Lys Thr
                820                825                830
Cys Val Lys Gln Cys Asn Asn Lys Glu Asn Asn Asp Gly Cys Gly Lys
                835                840                845
Asn Thr Gly Thr Asp Lys Arg Asn Thr Lys Asp Gly Asn Asp Thr Glu
    850                855                860
Thr Gly Asn Asn Gly Asn Asn Glu His Ser Gly Asn Asp Gly Asp Ser
865                870                875                880
Gly Asn Asn Gly Ser Lys Asp Lys Asn Ser Ser Gly Ser Gly Asp Asn
                885                890                895
Asn Asp Asp Lys Lys Asn Asp Asp Lys Asp Lys Lys Asn Asn Arg Asn
                900                905                910
Asn Lys Asp Gln Asp Lys Glu Arg Lys Lys Lys Asn Asp Met Lys Lys
                915                920                925
Gly Pro Gln Lys Asn Ser Ala Asp Asn Ala Asp Asn Thr Asp Arg Asp
    930                935                940
Gly Thr Asn Lys Thr Asn Asp Asn Asn Asp Asn Lys Asn Asn Glu Asn
945                950                955                960
Asp Glu Asp Lys Glu Glu Lys Glu Asn Lys Glu Asn Thr Glu Lys Ile
                965                970                975
Glu Thr Asn Gly Asn Asp Glu Asn Thr Cys Lys Lys Arg Lys Cys Gly
                980                985                990
Lys Gly Leu Thr Arg Asn Arg Asn Lys Gly Lys Asn Leu Asn Glu Asn
                995              1000               1005
Thr Thr Asn Ile Met Cys His Lys Thr Asp Glu Thr Cys Ser Ile
    1010               1015               1020
Asn Val Asp Ser Pro Leu Leu Asn Val Glu Lys Lys Tyr Pro Val
    1025               1030               1035
Lys Arg Arg Lys Glu Asn Lys Ile Asp Arg Lys Asn Tyr Asn His
    1040               1045               1050
Glu Lys Asn Glu Lys Tyr Ser Leu Asn Met Leu Ile Ala Glu Asn
    1055               1060               1065
Ala His Lys Ile Ile Lys Asn Gly Arg Val Tyr Lys Gln Phe Glu
    1070               1075               1080
Pro Cys Tyr Asn His Lys Thr His Asn Asn Phe Met Leu Lys Glu
    1085               1090               1095
Leu Leu Trp Met Ser Ile Asp Phe Tyr Glu Glu Lys Arg Trp Lys
    1100               1105               1110
Lys Asn Ile Ser Lys Arg Phe Ser Tyr Leu Met Asn Thr Asn Phe
    1115               1120               1125
Tyr Glu Lys Gln Lys Asn Asp Lys Tyr Phe Ile Ser Ser Gln Ile
    1130               1135               1140
Ser Asn Asp Ile Lys Met Phe Trp Phe Phe Ile Leu Asn Glu Ile
    1145               1150               1155
Arg Pro Asp Leu Val Pro Ile Asp Leu Asp His Lys Val Lys Asn
    1160               1165               1170
Lys Asn Gly Ile Lys Lys Asn Leu Phe Arg Ile Ile Lys Lys Asn
    1175               1180               1185
Ile Glu Ser Glu Glu Tyr Asn Phe Ile Asn Val Thr Asn His Ile
    1190               1195               1200
```

```
Asn Leu Asn Thr Asn His Asn Glu Leu Asn Ser Lys Gln Leu Gly
    1205                1210                1215

Ile Val Ser Arg Gly Glu Arg Glu Asn Asn Gly Asp Lys Asn Glu
    1220                1225                1230

Asn Lys Asp Gln Phe Leu Asn Ser Glu Asn Glu Asp Thr Ile Ile
    1235                1240                1245

Pro Lys Thr His Ser Gly Ile Phe Asn Lys Ile His Ser Leu Asn
    1250                1255                1260

Ile Leu Asn Glu Lys Asn Met Asn Pro Asp Glu Thr Thr Ser Lys
    1265                1270                1275

Asn Asp Asn Asn Ser Asn Asp Leu Asn Ile Leu Pro Lys Thr Asp
    1280                1285                1290

Asn Asn Ile Ile Glu Glu His Cys Gln Asn Leu Gly Ser Asn Asp
    1295                1300                1305

Lys Thr Val Lys Val Cys Lys Asn Asp Asn Asn Glu Phe Glu Asn
    1310                1315                1320

Gly Leu Thr Ser Tyr Glu Glu Cys Leu Ala Lys Leu Glu Asn Ser
    1325                1330                1335

Val Asn Lys Glu Met Leu Asn Lys Tyr Glu Tyr Asn Ser Lys Ile
    1340                1345                1350

Cys Tyr Asn Asp Ser Lys Asn Cys Asn Lys Ile Asn Glu Ile Ser
    1355                1360                1365

Tyr Lys Asn Thr Phe Tyr Tyr Asn Glu Glu Tyr Ser Asp Tyr Tyr
    1370                1375                1380

Asp Asn Asn Asn Asp Arg Lys Tyr Asn Val Ala Tyr Asn Gly Ile
    1385                1390                1395

Cys Asn Asp Phe Arg Tyr Tyr Asn Asn His Leu Gly Asn Asn Ile
    1400                1405                1410

Tyr Cys Asn Asp Cys Asn Tyr Leu Asp Leu Ser Asp Gln Leu Tyr
    1415                1420                1425

Ile Tyr Cys Leu Leu Phe Ile Ser Ile Ser Leu Ile Glu Ile Lys
    1430                1435                1440

Glu Asn Ile Phe Tyr Asn Ile Asp Asn Ile Ser Asn Glu Asp Lys
    1445                1450                1455

Val Thr Ile Leu Asp Glu Glu Asn Asn Thr His Ile Ser Lys Ala
    1460                1465                1470

Thr Tyr Ser Lys Ile Tyr Ala Lys Asp Asn Phe Glu Asn Glu Asp
    1475                1480                1485

His Gln Thr Thr Ser Gly Asp Asp Asn Val Lys His Gly Asp Ile
    1490                1495                1500

Asp Gln Ser Asn Asp Ser Gly Lys Asn Asn Asn Tyr Ile Cys Asn
    1505                1510                1515

Gly Lys Met Glu Lys Asn Glu Glu Asn Ile Asn Cys Asp Gly Lys
    1520                1525                1530

Asp Lys Met Ser Ile Glu Cys Lys Glu Asn Glu Ile His Ala Asn
    1535                1540                1545

Asp Gly Tyr Asp His Asn Asp Glu Asn Arg Lys Asn Glu Cys Lys
    1550                1555                1560

Lys Ile Glu Gly Asn Ile Asn Gln Leu Ser Glu Val Thr Glu Lys
    1565                1570                1575

Ile Asn Glu Asn Lys Ile Leu Lys Met Ile Lys Lys Glu Ser Lys
    1580                1585                1590
```

```
Asn Ser Thr Glu His Tyr Ser Asp Lys Pro Tyr Lys Glu Tyr Lys
    1595                    1600                1605

Ile Asn Gln Asn Gly His His Lys Ser Tyr Asn Ile Tyr Asp Asn
    1610                    1615                1620

Ala Asn Asp Glu Gly Tyr Lys Phe Asn Lys Asn Tyr Gln Asp Tyr
    1625                    1630                1635

Tyr Asp Asp Leu Lys Ser Asn Val Ser Tyr Arg Asn Asn Asn Asn
    1640                    1645                1650

Ser Asn Asn Ile Leu Pro Phe Ile Pro Ser Leu Ser Asn Ile Asp
    1655                    1660                1665

Ile Lys Glu Leu Ile Val Ile Pro Tyr Ser Leu Pro His Asp Asn
    1670                    1675                1680

Ile Ile Asn Lys Glu Thr Thr Tyr Ser Leu Glu Ser Glu Arg Lys
    1685                    1690                1695

Ile Tyr Glu Tyr Leu Asn Glu Ile Lys Glu Arg Asn Ile Asn Ile
    1700                    1705                1710

Tyr Met Asn Asn Met Glu Ser Tyr Gly Gly Lys Ser Tyr Pro Phe
    1715                    1720                1725

Glu Phe His Asn Ile Asp Asn Tyr Tyr Asn Asn Ile Asn Leu Pro
    1730                    1735                1740

Leu Thr Lys Leu Thr Glu Tyr Asp Glu Tyr Thr Phe Phe Leu Tyr
    1745                    1750                1755

Leu Phe Tyr Ile Lys Asn Ser Pro Tyr Ile Leu Lys Lys Gln Ile
    1760                    1765                1770

Gln Lys Asp Lys Lys Arg Lys Arg Asp Leu Pro Asp Ile Thr
    1775                    1780                1785

Pro Pro Lys Lys Arg Ala Ser Arg Arg Lys Leu Asn Lys Glu Ser
    1790                    1795                1800

Gly Glu Lys Glu Ile Glu Ile Ile Arg Glu Ser Glu Lys Val Thr
    1805                    1810                1815

Asn Asn Thr Glu Glu Val Asp Ser Lys Gly Ile Ser Glu Ile Asn
    1820                    1825                1830

Leu Leu Gln Thr Asn Asn Asn Ser Ile Leu Ile Lys Gly Gly Glu
    1835                    1840                1845

Asn Lys Asn Phe Tyr Asn Asn Lys Leu Thr Ser Lys His Val Gly
    1850                    1855                1860

Glu Ile Lys Lys Glu Pro Gln Phe Ser Lys Asp Asn Thr Glu Lys
    1865                    1870                1875

Glu Ile Lys Leu Trp Lys Glu Arg Lys Leu Glu Trp Thr Asn Asp
    1880                    1885                1890

Glu Ile Asn Phe Leu Leu Ile Leu Ala Asn Thr Tyr Ile Asn Tyr
    1895                    1900                1905

Ile Asn Leu Asp Thr Ile Thr Gln Leu Met Asp Asn Asn Gly Ser
    1910                    1915                1920

Asn Ile Thr Ile Tyr Asn Asn Asn Asn Gln Asn Glu Ile Tyr Asn
    1925                    1930                1935

Ala Gly Asn Asn Asn Ile Thr Ile Lys Asn Thr Leu Glu Val Glu
    1940                    1945                1950

Tyr Ser Thr Thr Val Val Glu Thr Val Gln Lys Glu Lys Lys Thr
    1955                    1960                1965

Leu Thr Asn Glu Lys Asp Val Lys Lys Leu Ser Asn Ile Ser Lys
    1970                    1975                1980

Glu Thr Pro Asn Glu Cys Lys Ser Glu Ser Leu Glu Ile Leu Gln
```

-continued

```
            1985                1990                1995
Asn Ile Lys Met Asn Asn Leu Asn Asp Ser Ile Leu Ser Thr Glu
            2000                2005                2010

Gly Lys Leu Gly Asn Thr Asn Ile Ser Thr Pro His Phe Lys Lys
            2015                2020                2025

Asn Asn Glu Ser Asp Lys Thr Ile Glu Asp Met Asn Tyr Val Tyr
            2030                2035                2040

Tyr Ile Asn Trp Thr Ile Ile Ser Leu Ala Leu Thr Ser Tyr Asn
            2045                2050                2055

Lys Ile Asn Asn Ile Cys Glu Ile Ser Lys Ser Ala Glu Glu Cys
            2060                2065                2070

Arg Asp Lys Phe Leu Ser Leu Ala Lys Asp Asn Lys Tyr Lys Asn
            2075                2080                2085

Tyr Asn Ile Tyr Asn Leu His Glu Asn Asn Phe Ile Asn Ser Lys
            2090                2095                2100

Asn Asn Ile Asp Asn Lys Lys Ser Ser Arg Lys Leu Lys Phe Leu
            2105                2110                2115

Ser Ile Phe Ser Thr Thr Arg Thr Asn Thr Leu Ile Glu Ala Phe
            2120                2125                2130

Asn Lys Tyr Met Asn Lys Lys Ile Glu Lys Tyr Lys Leu Arg Lys
            2135                2140                2145

Met Ala Arg Thr Glu Lys Lys Met Glu His Gly Gln Glu Val Ile
            2150                2155                2160

Arg Ser Lys Ser Glu Met Leu Asn Glu Asp Lys Ser Ile Asp Gln
            2165                2170                2175

Ala Asn Tyr Ile Ile Lys Thr Asn Asp Leu Gly Asn Asn Ile Phe
            2180                2185                2190

Cys Asp Glu Ser Glu Gln Asn Glu Leu Leu Asn Asn Thr Leu Ala
            2195                2200                2205

Glu Glu Met Ala Gln Ser Asn Tyr Lys Gln Thr Ser Val Ser Ser
            2210                2215                2220

Asn Ser Ser Ser Lys Asn Asp Ser Met Arg Ser Asn Ile Gln Asn
            2225                2230                2235

Glu Ile Ser Glu Thr Leu Lys Asp Gly Ser Phe Phe Asn Asp Ile
            2240                2245                2250

Asn Leu Asp Thr Asn Met Asn Arg Lys Glu Asp Phe Ile Asn Asn
            2255                2260                2265

Leu Phe Lys Glu Val Ser Val Asn Asn Tyr Glu Thr Ser Glu Glu
            2270                2275                2280

Asp Ala Glu Cys Gly Glu Asp Ser Phe Phe Ser Tyr Ser Asp Val
            2285                2290                2295

Gly Tyr Cys Ser Ser Gly Glu Leu Tyr Asn Asn Lys Ser Ser Ile
            2300                2305                2310

Lys Leu Glu Asn Met Ile Asn Ile Leu Asp Asn Leu Asp Asn Arg
            2315                2320                2325

Glu Lys Leu Lys Ile Glu Asn Ser Gly Leu Arg Glu Ile Thr Asn
            2330                2335                2340

Phe Lys Val Lys Glu Ile His Asp Asp Ile Thr Glu Gly Arg Asn
            2345                2350                2355

Lys Ile Asn Asp Asn Cys Glu Phe Leu Asp Gly Asp Glu Lys Lys
            2360                2365                2370

Ile Tyr Asn Ile Asn Glu Gly Glu Ile Glu Asn Asn Val Asn Asp
            2375                2380                2385
```

```
Asn Lys Pro Asn Cys Phe Leu Asp Val Thr Asn Asp Leu Lys Ile
    2390            2395                2400
Asn Ile Lys Lys Asp Ser Gly Ile Thr Ser Asn Lys Ile Asp Asp
    2405            2410                2415
Asn Tyr Asp Asn Met Glu Leu Gln Thr Asn Glu Ser Asp Asn Tyr
    2420            2425                2430
Gln Thr Asn Asp Ser Asn Met Val Asn Asp Val Lys Ser Glu Ile
    2435            2440                2445
Tyr Lys Asn Asp Asn Asp Gly Phe Glu Ile Lys Ile Lys Cys Asn
    2450            2455                2460
Glu Asn Gly Ile Tyr Ser Asn Asn Ala Glu Asn Asn Asn Arg Asn
    2465            2470                2475
Glu Asn Ser Ser Tyr Lys Thr Trp Lys Tyr Ser Ser Asn Phe Ala
    2480            2485                2490
Gly Ser Met Ser Glu Leu Ile Cys Tyr Asp Lys Ile Lys Lys Ile
    2495            2500                2505
Leu Asn Thr Val Cys Lys Asn Lys Lys Asn Val Asn Glu Phe Ile
    2510            2515                2520
Ser Leu Leu Lys Asn Glu Tyr Ile Ile Lys Asn Pro Tyr Phe Leu
    2525            2530                2535
Lys Val Ile Gln Ile Phe Ile Asn Asn Val Lys Pro Val Ile Gly
    2540            2545                2550
Tyr Tyr Asp Asn Met Ile Asp Ser Val Asn Glu Lys Ser Asp Tyr
    2555            2560                2565
Ile Tyr Ser Asn Lys Glu Tyr Leu Lys Asp Leu Cys Lys His Lys
    2570            2575                2580
Ile Asp Lys Glu Phe Val Asn Phe Ile Arg Lys Ile Ile Glu His
    2585            2590                2595
Asp Lys Lys Gln Lys Asn Lys Tyr Ile Glu Lys Ile Thr Lys Thr
    2600            2605                2610
Ile Pro Tyr Gln Asn Asn Ile Asn Ser Asn Glu Leu Ile Ile His
    2615            2620                2625
Ser Pro Ser Asn Ser Tyr Asn Thr Val Lys Asn Leu Ser Thr Lys
    2630            2635                2640
Ile Leu Asn Tyr Val Pro Tyr Val Asp Asp Lys Lys Lys Gly Asn
    2645            2650                2655
Ile Lys Gln Met Ser Lys Arg Phe Asn Ser Lys Asn Leu Val Ser
    2660            2665                2670
Gln Ile Leu Leu Ala Asp Tyr Ile Val Asp Lys Leu Lys Thr Phe
    2675            2680                2685
Pro Ile Ser Asp Ser Leu Thr Ser Ile Tyr Asn Asn Lys Thr Ile
    2690            2695                2700
Asp Glu Leu Ile Ser Glu Tyr His Leu Lys Ala Tyr Thr Glu Tyr
    2705            2710                2715
Ile Asn Asp Asn Phe Asn Glu Asn Asn Tyr Ala Ser Lys Leu Glu
    2720            2725                2730
Lys Ser Tyr Ile Asp Asp Pro Ser Thr Glu Ile Asn Asp Glu Ser
    2735            2740                2745
Ser Ile Asn Val Ser Leu Val Asp Ile Lys Asn Lys Asn Val Ser
    2750            2755                2760
Asp Val Met Lys Asn Asn Glu Asn Glu Leu Glu Gly Lys Phe Glu
    2765            2770                2775
```

```
Ile Ser Lys Lys Leu Ser Glu Asn Phe Gly Arg Thr Leu Pro Cys
2780                2785                2790

Asp Gln Thr Ser Lys Lys Glu Asn Ser Leu Tyr Asn Lys Thr Thr
2795                2800                2805

Gly Asp Lys Thr Glu Asn Thr Phe Asn Ile Leu Pro Thr Phe Gly
2810                2815                2820

Asn Asn Thr Pro Asn Asn Lys Phe Ala Asn Asn Asn Asn Thr Asn
2825                2830                2835

Thr Asn Thr Asn Asn Tyr Asn Asn Asn Glu Thr Ile Asp Ser Ile
2840                2845                2850

Ser Glu Asn Val Thr Asp Ala Asn Leu Cys Val Asn His Glu Lys
2855                2860                2865

Asn Ile Glu Met Asp Ala Lys Thr Ser Ser Asn Met Thr Leu Gly
2870                2875                2880

Ile Leu Glu Asn Ser Lys Asn Asn Thr Asn Ile Asn Ser Asp Asn
2885                2890                2895

Val Leu Asn Asn Asn Asn Thr Pro Asn Asp Asn Asn Gln Gly Leu
2900                2905                2910

Lys Lys Leu Lys Lys Val Asn Ser Glu Pro Ser Val Asn Leu Tyr
2915                2920                2925

Asn Asp Lys Ile Ile Asp Leu Gly Asn Tyr Thr Lys Gln Ile Lys
2930                2935                2940

Asn Ser Ser Lys Thr Gln Pro Ile Arg Lys Asn Thr Gly Thr Thr
2945                2950                2955

Asn Lys Ile Thr Lys Tyr Lys Thr Ser Thr Asn Leu Cys Asn Tyr
2960                2965                2970

Ser Asn Ile Lys Gly Arg Lys Asn Asn Asn Asn Asp Asn Asn
2975                2980                2985

Asn Asn Asn Asn Asn Asn Asn Asn Asn Asn Asn Asn Asn Asn
2990                2995                3000

Asn Asn Asn Asn Asn Asn Asn Asn Asn Asn Asn Asn Asn Asn
3005                3010                3015

Asn Asn Asn Asn Asn Asn Asn Asn Asn Asn Asn Asn Asn Asn
3020                3025                3030

Asn Asn Ser Asp Asn Asn Ile Ile Leu Asn Cys Ala Gln Asn Ile
3035                3040                3045

Lys Trp Pro Ser Leu Asn Lys Phe Glu Thr Gln Thr Asn Pro Thr
3050                3055                3060

Asn Asn Asn Asn Asn Asp Tyr Asn Asn Phe Tyr Lys Glu Gly Thr
3065                3070                3075

Pro Val Phe Glu Gln Leu Pro Ile Ser His Glu Glu Ser Asn Asn
3080                3085                3090

Asn Gln His Met Cys Asn Glu Lys Ile Asn Leu Thr Arg Lys Lys
3095                3100                3105

Gln Lys Ala Ser Asp Asn Lys Cys Asn Asn Ser Ile Lys Asn Val
3110                3115                3120

Ala Asn Glu Asn Leu Asn Lys Tyr Pro Ser Asn Gln Pro Tyr Tyr
3125                3130                3135

Gln Val Lys Asn Ile His Asp Asn Tyr Phe Asn Asp Asn Asn Gln
3140                3145                3150

Thr Pro Met Lys Leu Asn Thr Arg Ile Pro Ser Thr Asp Ile Ser
3155                3160                3165

Ile Ile Pro Ser Ser Ala Thr Met Cys Glu His Ile Lys Cys Ser
```

```
              3170            3175            3180
Asp Asn Ser Asp Leu Ala Asn Arg Thr Asp Leu Leu Cys Asn Gly
        3185            3190            3195

Ser Gln Pro Gly Asn Asn Val Pro Leu Asn Ile Ile Asn Ser Asn
        3200            3205            3210

Ser Ser Ser Ser Asn Gly Ile Ser Asn Lys Asn Ile Gly Leu Asn
        3215            3220            3225

Ser Ser Ser His Leu Asn Asn Val Gly Gly Met Ile Val Gly Gly
        3230            3235            3240

Met Asn Ser Ser Asn Asn Asn His Ile Ile Asn Asn Phe Ala His
        3245            3250            3255

Lys Gly Gly Glu Glu Gly Asp Lys Phe Thr Pro Phe Ser Tyr Gly
        3260            3265            3270

Ala Leu Gln Asn Asn Lys Tyr Val Ser Pro Ser Gln Gly Asn Asn
        3275            3280            3285

Gln Ile Tyr Tyr Asn Lys Ala Pro Ile Tyr Glu Ser Pro Asp Ile
        3290            3295            3300

Ala Ser Asn Lys Ile Gly Gly Asn Asn Thr Met Asn Thr Tyr Asn
        3305            3310            3315

Ser Arg Ser Ala Asp Ile Ser Ser Asn Tyr Phe Asn Ser Arg Leu
        3320            3325            3330

Leu His Ser Leu Ser Asn Ser Asn Asn Leu Asn Asn Val Asn Leu
        3335            3340            3345

Asn Val Asp Lys Asn Gly Tyr Ser Ala Asn Met Arg Asp His Ile
        3350            3355            3360

Gly Ile Ser Arg Arg Ser Ser Thr Ser Ile Leu Cys Ser Glu Thr
        3365            3370            3375

Asn Glu Asn Asn Glu Asn Val Ile Phe Met Lys Ser Arg Ser Pro
        3380            3385            3390

Ser Asn Tyr Pro Ser Pro Tyr Asn Pro Asn Lys Gly Ile Met His
        3395            3400            3405

Asp Asn Asp Ser Ser Lys Ser Tyr Tyr Asp Ser Gln Ile Leu Gln
        3410            3415            3420

Gln His Met Gln His Gln Thr His Gln Ser Ala Gln Gln Gln Ser
        3425            3430            3435

Gln Ile Ile Ser Asn Thr Asp Ile Val Asn Asn Met Ala Met Ser
        3440            3445            3450

Thr Asn Asn Gly Leu Thr Asn Asn Lys Glu Glu Ser Asn Asn Asp
        3455            3460            3465

Pro Ser Asn Ile Ser Glu Ala Lys Asn Lys Asn Val Ile Tyr Gln
        3470            3475            3480

Asn Tyr Ala Leu Asn Lys Tyr Pro Ser Asn Ser Val Lys Lys Leu
        3485            3490            3495

Ser Gln Ile Asn Asn Gln Asn Asp Ser Asn Ile Gln Pro Gly Tyr
        3500            3505            3510

His Asn Ile Asn Tyr Asp Gln Ile Asn Asn Tyr Ile Pro Gln
        3515            3520            3525

Asn Leu Met Lys Asn His Asn Glu Leu Leu Ser Ser Asn Asn Asp
        3530            3535            3540

Lys Lys Gln Met Val Tyr Tyr Pro Thr His Pro Ile Pro Asn Phe
        3545            3550            3555

Ala Asn Ile Asn Asn Val Pro Leu Glu Asn Leu Asp Lys His Asn
        3560            3565            3570
```

```
Ile Ala Phe Ser Asn Glu Ser Phe Asn Arg Asn Ile Asn Tyr Leu
3575                3580                    3585

Asn Gln Ile Asn Leu Val Lys Leu Asp Pro Val Ser Glu Lys Glu
3590                3595                    3600

Asn Met Asn Thr Gly Ala Lys Ile Val Gly Glu Lys Val Gln His
3605                3610                    3615

Thr Gln His Ser Ile Lys Asn Asn Thr Gln His Ser Asp Ile His
3620                3625                    3630

Asn Ser Ile Ile Glu Asn Asn Leu Gly Gln Ser Asn Tyr Ala Val
3635                3640                    3645

Asn Met Ile Asn Gly Gly Ser Leu Ser Ser Ser Ser Asn Val Leu
3650                3655                    3660

Ile Glu Gly Thr Pro Asn Asn Asp Ile Asn Ala Asp Val Asn Asn
3665                3670                    3675

His His Asn Leu Ser His Ile Pro Ser Ile Ser Met Gln Gln Ser
3680                3685                    3690

Gln Ile Asn Ile Asp Gln Asn Asn Asn Tyr Ile Ser Asn Glu His
3695                3700                    3705

Glu Arg Asp Ser Ala Ser Arg Met Gln Phe Thr Pro Lys Gly Ser
3710                3715                    3720

Ala Ile Pro Val Pro Asn Gln Gln Asn Ile Asn Ile Asn Asn Gln
3725                3730                    3735

Gly Ile Lys Tyr Asn Glu Ile Asn Val His Asn Ile Lys Gln Pro
3740                3745                    3750

Asn Asn Leu Asn Ser Tyr Ile Asn Gln Val Asn Phe Ile Val Gln
3755                3760                    3765

Val Leu Asn Lys Lys Lys Cys Asn Gln Thr Asp Asn Ile Pro Pro
3770                3775                    3780

Asn Ile Asn Gln Gln Thr Met Gly Lys Tyr Asn Val Asp Gln Thr
3785                3790                    3795

Val Val Asn Thr Leu Asn Leu Lys Gln Gly Asn Phe Ala Asn Pro
3800                3805                    3810

Asn Leu Ser Gln Pro His Asn Asn Asn Ile Ile Gln Asn Gly Asn
3815                3820                    3825

Asn Asn Asn Asn Asn Met Gly Leu Ser Thr Tyr His Thr Gln Pro
3830                3835                    3840

Asn Thr Asn Leu Lys Asn Ile Lys Pro Pro Met Asn Asp Ser Asn
3845                3850                    3855

Ile Ser Asn Met Leu Asn Met Gly Met Arg Asn Asn Met Ser Lys
3860                3865                    3870

Asn Ile Ile Ser Asn Ile Pro Pro Asn Asn Val Phe Ser Ala Lys
3875                3880                    3885

Asp Val Ile Gln Gln Lys Ile Leu Gln Gln Gln His Lys Met
3890                3895                    3900

Gln Gln Glu Leu Ile His Lys Ser His Asn Asp Lys Asp Asn Leu
3905                3910                    3915

Val Asn Pro Arg Met Gln Phe Ser Glu Glu Gln Met Gln His Gln
3920                3925                    3930

Lys Leu Leu Gln Lys Met Lys Gln Glu Gln Leu Gln Lys Pro Leu
3935                3940                    3945

Gln Gln Ile His Pro His Gln Met Gln Thr His Asn Met Asn Ser
3950                3955                    3960
```

```
Gln Gln His Met Tyr Ile His Pro Met Gln Gln Lys Met Gln Ala
    3965                3970                3975

Leu Gln Ile Gln Ser Leu Leu Lys Ala Gln Gln Ile Lys Lys Gln
    3980                3985                3990

Leu His Pro Ser Gln Leu Gln Gln Gln His Met Gln Gln Lys Leu
    3995                4000                4005

His Pro Gln Gln Ile His Pro Gln Gln Leu Arg Ser Pro Gln Ile
    4010                4015                4020

Pro Gln Gln Gln Ile Thr Pro Gln Gln Ile Gln Gln Ile Gln Gln
    4025                4030                4035

Met Lys Met His Asn Ile Gln Phe Lys Lys His Glu Met Lys Lys
    4040                4045                4050

His Met Glu His Leu Gln Lys Asn Ile Pro Tyr Asn Gln Gln Gln
    4055                4060                4065

Ile His Gln Ile Tyr Asn Leu Gln Gln Asn Ile Ser Asn Asp
    4070                4075                4080

Glu Thr Asn Asp Lys Gln Asn Met His Leu Gln Ile Ser Met Gly
    4085                4090                4095

Ile Asn Pro Lys Ile Gln Asn Met His Met Leu Gln Ala Lys Asn
    4100                4105                4110

Asn Asp Glu Leu Ile Ser Lys Glu Asn Leu Asn Asn Leu Asn
    4115                4120                4125

Glu Asn Pro Ile Tyr Ala Val Asn Arg Thr Phe Ser Asn Asn Ile
    4130                4135                4140

Asn Lys Phe Lys Asn Pro Asp Asn Phe Tyr Ser Gln Asn Ser Phe
    4145                4150                4155

His Pro Thr Pro Ser Ser Asn Lys Met Asp Leu Lys Asp Ile Arg
    4160                4165                4170

Ser Ile Gly Asn Lys Thr Leu Ile Glu Asn Asn Ile Ala Leu Asn
    4175                4180                4185

Pro Ser Gln Lys Arg Ala Asp Ile Ser Asn Asn Asn Ile Ala Pro
    4190                4195                4200

His Ile Leu Pro Ile Asn Met Ala Ser Tyr Asn Ser Gln Asn Met
    4205                4210                4215

Gln Cys Lys Ile Asn Ile Lys Asn Asn Ser Asn Ser Gln Glu
    4220                4225                4230

Asn Asn Cys
    4235

<210> SEQ ID NO 3
<211> LENGTH: 14
<212> TYPE: PRT
<213> ORGANISM: Plasmodium berghei

<400> SEQUENCE: 3

Ile Ser His Asn His Asn Asp His Ile Met Glu Glu Asp Val
1               5                   10

<210> SEQ ID NO 4
<211> LENGTH: 14
<212> TYPE: PRT
<213> ORGANISM: Plasmodium berghei

<400> SEQUENCE: 4

Met Lys Lys Gly Pro Gln Lys Asn Ser Ala Asp Asn Ala Asp
1               5                   10
```

<210> SEQ ID NO 5
<211> LENGTH: 14
<212> TYPE: PRT
<213> ORGANISM: Plasmodium berghei

<400> SEQUENCE: 5

Pro Pro Lys Lys Arg Ala Ser Arg Arg Lys Leu Asn Lys Glu
1               5                   10

<210> SEQ ID NO 6
<211> LENGTH: 14
<212> TYPE: PRT
<213> ORGANISM: Plasmodium berghei

<400> SEQUENCE: 6

Asn Leu Thr Arg Lys Lys Gln Lys Ala Ser Asp Asn Lys Cys
1               5                   10

<210> SEQ ID NO 7
<211> LENGTH: 2358
<212> TYPE: DNA
<213> ORGANISM: Plasmodium berghei

<400> SEQUENCE: 7

| | | | | | |
|---|---|---|---|---|---|
| atggctaata | aaatatataaa | taatcagaaa | attcaaaagg | atgaaaataa | aaaaaagaat | 60 |
| gatgaatctg | aagtttgtaa | ttttcatgaa | gtaaatatat | cgtataaaaa | atgggttaaa | 120 |
| gataaaatac | aacaacaaaa | aataactttg | tttaatttaa | aaaaatacaa | tctttctaaa | 180 |
| aaacaaaaaa | gtatcaatat | tatatctttt | attactattc | ttatattatt | aaatataatt | 240 |
| tataatcggt | tgattgatat | ttggtataat | tgggatgaaa | aatagaaaa | ttttgatgaa | 300 |
| actaaaaaat | gtgaaaataa | aaatgattat | aattttaata | aatatataag | acaatgtagt | 360 |
| aatttttga | aatatttaat | gaagggggtca | cttgatgaag | atatatatga | tgataataat | 420 |
| ttagaaaatg | atttcatata | tataaaaaat | tctaaaagta | gaaatacaat | atatttaaaa | 480 |
| aaatatattag | gaagtgaaat | tattgataat | aattatataa | gtgtgtattt | agaaaatatg | 540 |
| aaatatttaa | gaaatacaag | tttaaattat | tctgtaaatc | aaagatcgct | gtctacagaa | 600 |
| tggtatgttt | attttcgtag | ttttttaaaa | caagctataa | cacccccatag | tttaacaaaa | 660 |
| gctataaaaa | ttgataaaga | atatatatat | ccttgggatg | taataactca | ggatgatgct | 720 |
| gaaaaaatta | ttgaaaatgc | caaattttat | ggttttttgt | ttacatggtt | taaaaatcat | 780 |
| agaaaagcac | aaaaagtgaa | tgaaataatt | ttaagaaaag | atatgcctgt | tttaattcct | 840 |
| aagtttataa | aatcagattt | ttctcaacgc | ttatacaaaa | atagtaaaaa | taatgaaccc | 900 |
| aatttttatg | gaatacatta | tacatggtta | gggcatgcaa | caggtttagt | tattgtagat | 960 |
| ggacttaaaa | tattagttga | tcctgttttt | aaaatcgaat | tattaagtct | taaaggaata | 1020 |
| gcacgatctt | taataaattg | ggtgaatata | aaaataatgg | gaggattggg | ggaacgaata | 1080 |
| tcaaaatcgc | catgtaatat | ttcaaatctc | cctgatgatt | tacatgctgt | ttttattca | 1140 |
| cataatcata | atgatcatat | aatggaagaa | gatgtacgaa | ttttatgtaa | attaaaaaaa | 1200 |
| tttaagatg | ttatgtggta | tgttccagaa | ggtacaactt | catttttat | acaagaaggt | 1260 |
| tgtaaaactg | ataaaattta | tgaattatct | tggggtgatg | aacgatgggt | atcatgctgg | 1320 |
| ataaataata | ataaatttac | atgtaaagat | ggattatgga | ataacaaaaa | aggtgataca | 1380 |
| gatgtatata | aatataaaat | tatatatgcc | ccagcattac | attggtcagg | tagaaaagga | 1440 |
| gatttaagtg | atattaatca | atcattatgg | ggttcattaa | tattaaaagg | tcctaaatca | 1500 |

```
aaatttttatt tttctggtga tactgcatat ttaaaagatg attttgaaga atttaaaaaa    1560
attggaaaac tacatggacc attcgatttt gctgctatat ctataggagc atatgaacca    1620
aacaattcat taaaatatca tcatatacat ccatgggaat ctgtaaaaat atggagagat    1680
attcgagctg aaatagctat tgggatacat tggggtactt ttcgtctttc tgccgaagaa    1740
tttttacaac cccgggatga cttagaagct gctttattag gagttagttt aaatacttta    1800
agaaattata atcttacatt tgaaaaaaaa aagatggaaa ttttaaaaaa atatatggta    1860
aaaaatgtaa attcaaataa taatgatatt gatgatttag aagatttaaa agaatatttt    1920
tatcctgctt cttcaacaga ttataatgaa atacagata gttttcattc tattttttct    1980
aataatttaa gtttatttta ttcagatatt gataaaaatt atataaaaca tatgtaccaa    2040
caaaaaaaat tatatttgtc tactataat agatataaaa gagcattaat attaaaaaat    2100
tcaaagaaat taccaaaatc ttggaaaaaa ttattactca atctttcgat tcgatttcaa    2160
acaatcccta ttggtggatc catagaaatt aaaacaaaag ataacacaat ttcaatgact    2220
cgatcatctg aatataattc tactattat gagcattaca catttccaaa atggtataaa    2280
aaaaaagaaa aagaagaaac tctttatcaa tataactttc cacatgaaga tttgatgaca    2340
ttttctatag ttaactaa                                                 2358

<210> SEQ ID NO 8
<211> LENGTH: 12711
<212> TYPE: DNA
<213> ORGANISM: Plasmodium berghei

<400> SEQUENCE: 8
atgagcactg tcgaagacaa aatggatatt aaccaaaaca atgtggattt gtgtaagtat      60
tataagaata ataataccaa taacagtgat gcttaaaaat atgatgacta ttttttttaga    120 gatttaaaaa aaaaaaattt gaattattat attaaaaagg ataattattg taaaataata    180
cttagtgatg aaagtaactt acaatatgtt aaatggatga ttgatttaat gaattacaac    240 aaatatataaa aagaaatatc acttcaagtt ttgttggata ttcaaaagat atgtaacagc    300
ataagtttat ttttttattaa aatatatatt catatctata tatacttata tgctttacgt    360
agattatatt tatccgtatt ttgcgttata ttaaaatatc tcattaaaaa atataaatgc    420
ataattttaa ataaaatagg ggatataaat aaaatcaaca atttatcaaa tataaaaaag    480
gtaaagggca tcgacaaaaa tgcatccaat gtaatattaa ttcatgaaat aaaatgttct    540
tcttactatg attggtataa aatagtgact aatgatcact tcgaaaaaaa tgggaaaaca    600
cattattaca gtagcttaat ttatcctaaa atgtatacag gaatactttt ggtttctaca    660
aataattatt attttgtttt aaataaaaat gttgatatta aaataatag caaaaaattg    720 ttaatgttgt tgatgaataa tatggtgaat tattgtcaaa tcgactatat tgagtatgtt    780
tatgtgtgta atgaaattaa caataaaaaa tatttaata aatgtgaaaa actaataat    840 aataaaaata atagtaaaat aatagtgtgc atatctaaga caaatcgaaa tttcataata    900
gtagcttata atattaataa aagaattat ccatgtataa aaatatttg tggatttata    960 gaaaaacaaa gatgctataa tgcgccatca tattataaaa atatgtgcga aaaatttac    1020 actaatgata taataacaa caatattagc tttagtcata ttaaatacta tttaaagctt    1080
gacacaaaaa ttaaaaatc aaaaaaaatc aaaaattcgc tttttgattt tagggaaaat    1140
gaaaaccaaa gcggttatat tatttataag attcctaata atttatgtaa aaaaagggaa    1200
```

```
atttcaaaaa tgtataatat aaaatgtaat atactctatg tttattattt ttttgccacg   1260
agacaaaaaa atatagttag tgaaatatta tattattcct cttgtaaaaa tttaacaaaa   1320
ggaatttatt atgaagattt tcatctacta ttttttctta ttaaaaaatt gtatattttc   1380
agaaaacctt tgttggttat atgcttaaac aattttgaag taataaacct ttttatttca   1440
gattctatta atgttatata ctgttacaaa gcatttataa aaaaatatat tttgtcaaaa   1500
aaatataata ttataagtaa aatggatgta atgactacat attattatat acactttaat   1560
ttatcaaaag aaagaaatat ttatcataca aaaataaatc acattttact aaatatgtta   1620
aacggacgga tctgcaaaaa atatgttata aaattttgca ctgaagattg tatgaaaata   1680
tgttcagagt attacataat aataactctt ttgaagcttt atgcaaagta ttttcgcaca   1740
tttataaata gcaattttga ttttttcggt ttgttaaatt gtaatattaa ttttataaat   1800
atctctaatg acgataatat taatggtatt gtgaataata atagagacac taataatagt   1860
ataaattttc atcgttctac aaattactcc agatcaattt taagaaaaaa acgaggaaaa   1920
aatagacacc tgcacaattt acaaaaatat gcatatttta taattttta caatattgtg   1980 ttacatgtga aaaataaacc tattaaaaaa ataaatatac tattttcaga aaaagactca   2040
ttatatgtta taaaaaagct aaataattac gtgaaaaaaa aaaaaaaatt tatattatat   2100
tatatatata ataatattga tattttttt ataagagcta atttcaagtc aaatatacga   2160
agaaatatat ttttaaaat aataataaaa tatattaaaa atgttgaaaa attaaaaga   2220 tatggtgaaa tttgctttt tagtaaaatt ataaatcttg aatttattca caaaaggtc   2280 ataaacacct tttttttcat atcaaaaaaa tgctataagt ttaaatatta taataattta   2340
actaaatata tatatatatt tttttttttg ataataaaat gtaatgaaga attatattca   2400
aaatataaaa gcatgaatat aatacgtaat gaacttaaag aagaaaaata tatagaaaat   2460
agtgaaaaaa atttagtaa catatttatg aaaacatgtg ttaaacagtg taataataaa   2520
gaaaacaatg acggttgcgg aaaaaatact ggaacagata aaagaaacac aaaagatggt   2580
aatgatactg aaacgggaaa taatggaaat aacgaacata gtggaaatga tggcgatagt   2640
ggaaataacg gtagtaagga taagaatagc agcggtagtg gggataataa tgatgataaa   2700
aaaaatgatg ataaagacaa aaaaaacaat agaaacaata aggatcagga taaagaacgg   2760
aaaaaaaaaa atgatatgaa aaagggacca caaaaaata gtgctgataa tgctgataat   2820
actgatagag acggaaccaa caaaaccaat gataataatg acaataaaaa taacgaaaat   2880
gatgaggata aagaggaaaa agaaaataaa gagaatacag agaaaataga aaccaatggg   2940
aacgatgaaa atacttgtaa gaaaagaaag tgcggaaagg gtctaacgag aaatagaaac   3000
aaagggaaaa atctcaatga aaacactaca aatataatgt gtcataaaac agatgaaaca   3060
tgctcaatta atgttgattc gccgctatta aacgttgaaa aaagtatcc cgtgaaaaga   3120 agaaaagaaa ataaaataga tagaaaaaat tataatcatg aaaaaaatga gaaatattca   3180
ttaaatatgc ttattgctga aaatgcacat aaaattataa aaaatggaag agtatataaa   3240
cagtttgaac cttgttataa tcataaaaca cataacaatt tcatgctaaa agaattgtta   3300
tggatgagta ttgatttta tgaagaaaaa aggtggaaaa aaacatatc aaaaagattt   3360 agctatctta tgaatactaa ttttatgaa aaacaaaaaa atgataaata ttttatatct   3420
tctcaaatat caaacgatat aaaaatgttt tggttttta tattaaatga ataagaccct   3480
gatttagttc caatagattt agatcataaa gttaaaaata aaaatggtat aaaaaagaac   3540
ctatttcgta ttattaaaaa aaatatagaa tctgaagaat acaatttat aaatgtaaca   3600
```

```
aaccatatca atttaaatac taatcataac gaactaaaca gtaaacagtt aggaattgtt    3660
agtagaggtg aaagagaaaa caatggagat aaaaatgaaa ataaagatca atttttaaat    3720
tctgaaaacg aagatacaat aatccccaaa acgcattctg gtatattcaa caaaatacat    3780
tctctgaata tattaaatga aaaaaatatg aaccctgatg aaacaacatc aaaaaatgat    3840
aataattcaa atgatttaaa tattctccca aagaccgaca ataatataat tgaagaacat    3900
tgtcaaaact taggaagtaa tgataaaact gttaaggttt gtaaaaatga taataatgaa    3960
tttgaaaacg gattaacgtc ttatgaagaa tgcttagcaa aattagagaa tagtgtaaac    4020
aaggaaatgc tgaataagta tgaatataat agtaaaattt gttataatga ttcaaaaaat    4080
tgtaataaaa taaatgaaat cagttataaa aatacatttt attataatga agaatatagt    4140
gattactatg acaataataa tgatagaaaa tataacgtag cgtataatgg gatatgtaat    4200
gattttagat attataataa tcatttggga aataatattt attgtaacga ttgtaattat    4260
ctcgatttaa gtgatcaatt atacatatat tgcttacttt ttataagtat ttctctaatt    4320
gaaattaaag aaaatatatt ttataacatt gataatattt caaatgagga taaagtaaca    4380
atattagacg aagaaaataa tacgcatatt tcgaaggcaa catattcaaa gatatatgcc    4440
aaagataatt ttgaaaatga agaccatcaa acaacatcag gggatgataa tgtcaaacat    4500
ggagatatcg atcaaagtaa tgatagtggc aaaaataata actatatttg taatggaaag    4560
atggaaaaaa atgaagaaaa tattaattgt gatggaaaag ataaaatgag cattgaatgt    4620
aaagaaaatg agatccatgc taatgatgga tatgatcata atgatgaaaa tagaaaaaat    4680
gaatgtaaaa aaatcgaagg aaatattaat cagttatccg aagtcacaga aaaaataaat    4740
gaaaataaaa ttttaaaaat gataaaaaaa gaaagcaaaa acagcacaga acattatagt    4800
gataagccat ataagaata taaaattaat caaaatgggc atcataaaag ttataatatt    4860
tatgataatg caaatgatga aggttataaa tttaataaaa attaccaaga ttattatgac    4920
gatttaaaat cgaatgtaag ttatagaaat aataataaca gtaacaatat tctaccattt    4980 atacctcgt taagtaatat agacataaaa gaattaatag taattccgta ttcgttacca    5040
catgataata taataaataa agaaacaaca tatagtttag aatcagaaag aaaaatatat    5100 gaataccta atgaaataaa ggaaagaaat ataaatatat atatgaacaa tatggaatca    5160
tatggaggta aatcttatcc ttttgaattt cataatatag ataattatta taataatatt    5220
aatttaccat tgaccaaatt aactgaatat gatgaatata cctttttctt gtatttattt    5280
tatataaaaa attcgccata tattaaaa aaacaaatac aaaagataa aaaaaaacgg    5340 aaacgtgatt tgccagatat tactccacca aaaaaagag cttctagacg taagctaaac    5400
aaagaaagcg gtgaaaaaga atcgaaata attcgagaat ctgaaaaagt tacaaataat    5460
acagaagagg ttgattcaaa gggaatatcc gaaataaatt tattgcaaac aaataataat    5520
tcaatactaa taagggggg agaaaataaa aactttata ataataaatt aactagtaaa    5580
catgtaggtg aaataaaaaa agaacctcaa ttctctaaag ataatactga aaggaaata    5640 aaattatgga agaaagaaa attagaatgg acaaatgatg aaattaattt tttattaatt    5700
ttggcaaata cttatataaa ttatataaat ctcgacacga ttcacagtt aatggataat    5760 aacgggtcga atattactat ttacaataat aataatcaga atgaaattta taatgcgggg    5820
aataataata taacaataaa gaatactctt gaagtggaat actcaacgac cgtagtagaa    5880
accgttcaaa aagaaaaaaa aaccttaact aacgaaaaag atgtaaaaa acttagcaat    5940
```

```
atcagtaaag aaacaccaaa tgaatgcaaa tcagaaagct tggaaatttt gcaaaacatt    6000
aaaatgaaca atttgaatga ttcaatttta tctaccgaag gaaagttggg caatacaaat    6060
atctcaactc cccatttaa aaaaaataat gagagtgata aaacgattga agatatgaat     6120
tatgtttatt atattaattg gacaataata tcattggcat taacgtcata taataaaata    6180
aataacattt gtgaaatatc aaaagtgca gaagaatgcc gagataagtt tttatcttta     6240
gcaaaagata taaatataa aaattataat atatataatt tacacgaaaa taattttatt     6300
aattcaaaaa ataatataga taacaaaaaa agttcaagaa aattaaaatt tttatccata    6360
ttctcaacta cacgaactaa cacgttgatc gaagcttta acaaatatat gaataaaaaa    6420
atagaaaaat acaaactaag aaaaatggct cgtaccgaaa aaaaaatgga acatgggcaa    6480
gaagttataa gaagtaaaag tgaaatgcta aatgaagata aatcaatcga tcaagcaaac    6540
tatataataa agactaacga tttgggaaat aatattttct gtgatgaaag tgagcaaaat    6600
gaacttttga ataatacgtt agcagaagaa atggcacaat caaattacaa acaaactagc    6660
gtttcgagta atagtagtag taaaaatgat agtatgagga gtaatataca gaatgaaatt    6720
tctgaaacat taaaggatgg ctccttttt aatgatataa atttagatac gaatatgaac    6780
agaaaagaag attttataaa taattttattc aaagaagttt ctgtaaataa ttatgaaaca    6840
tctgaagaag atgcagaatg cggtgaggat agtttttttta gttatagtga tgttggttat    6900
tgttcatctg gggaattata taataacaaa tcatccataa aattagaaaa tatgataaat    6960
atactagata atttagacaa tagggaaaaa ctcaaaattg aaaatagcgg attaagggaa    7020
attacaaact tcaaagtaaa agaaatacat gatgatatta cagagggaag aaacaaaatt    7080
aatgataatt gtgaattttt ggatggagat gagaaaaaaa tatataacat aaatgagggt    7140
gaaattgaaa acaatgtaaa tgataataaa cctaattgtt tcttggatgt tacaaatgat    7200
ttaaagatta atataaagaa agattcagga attacatcaa ataaaataga tgataattat    7260
gataatatgg aattacaaac taacgaaagt gacaattatc aaacaaacga tagtaatatg    7320
gtgaatgacg tgaaatctga aatatataaa aatgataacg atggattcga aataaaaatt    7380
aaatgcaatg aaaatggtat atattcaaat aatgctgaaa ataataatag aaatgaaaat    7440
agttcttata aaacttggaa atattcatcc aatttttgcag gctcaatgag cgaattaatt    7500
tgttatgaca aaataaaaaa gattttgaat actgtatgta agaataaaaa gaatgtgaac    7560
gaatttatat cattactaaa aaatgagtat attataaaaa atccctattt tttaaaagta    7620
atacaaattt ttataaataa tgttaaacca gttattgggt attatgacaa tatgatagat    7680
tcggtaaatg aaaagtctga ttacatctat tcgaataaag aatatttaaa agatttgtgt    7740
aaacacaaaa tagataaaga atttgttaat tttataagaa aaataataga acatgataaa    7800
aaacaaaaaa ataagtatat cgaaaaaatt accaaaacaa ttccatatca aaacaatatt    7860
aactctaatg aattaattat acattctcct agcaattcgt ataataccgt taagaattta    7920
tcgacaaaaa ttcttaatta tgttccatat gtagatgata aaaaaaaagg aaacattaaa    7980
caaatgagca aacgattcaa cagtaaaaat ttggtatcgc aaatattatt agctgattat    8040
attgtagata aattaaaaac ttttccaatt agtgattcat taacatctat ttataataat    8100
aaaactattg acgagctaat atcagaatat catttaaagg catatacaga atatattaat    8160
gataatttta cgaaaacaa ttatgcatct aaattagaaa aatcatatat cgatgatccc    8220
tcgacagaaa taaatgatga atcatcgatt aatgtaagtt tagttgatat caaaaataaa    8280
aatgtatcag atgttatgaa aaataatgaa aatgaattag aaggaaaatt cgagataagc    8340
```

```
aagaagcttt ccgaaaattt tggacgcaca ttaccatgtg atcaaacttc taagaaggaa    8400
aattctttat ataacaaaac aacaggagat aaaactgaga atactttcaa tatattaccc    8460
acgtttggta ataatactcc aaataataag tttgccaata ataataatac taatactaat    8520
actaataatt ataataataa tgaaactatt gatagtatca gtgaaaacgt aactgatgct    8580
aatttgtgtg taaatcacga aaaaaatatc gagatggatg caaagactag cagtaatatg    8640
actttaggaa tattgaaaaa cagtaaaaat aacaccaata taaattctga taatgtactt    8700
aataataata acacaccaaa tgataataat caaggattaa aaagttaaa aaaggtaaac    8760 tctgagcctt cagtgaatct ttacaacgat aaaataattg atttgggaaa ctatacgaag    8820
caaataaaga attcttcaaa aacacaaccg atacgaaaaa acactggaac aactaataaa    8880
ataacgaaat ataaaacgtc cacaaatttg tgtaattatt caaatattaa gggtcgaaaa    8940
aataataata ataatgataa taataataat aataataata ataataataa taataataat    9000
aataataata ataataataa taataataat aataataata ataataataa taataataat    9060
aataataata ataataataa taataataat aataataata ataatagtga taataacatt    9120
atattgaatt gcgcacaaaa tataaaatgg ccatcattaa ataaatttga aacccaaaca    9180
aatccaacaa ataacaacaa caatgactat aataattttt ataagagggg tactcccgtt    9240
tttgaacaac tgcccatttc acatgaagaa tcaaataaca atcagcatat gtgtaacgaa    9300
aaaataaatt taacaagaaa aaaacaaaaa gcatcagata ataaatgtaa caattctatt    9360
aaaaatgtag caaatgaaaa tttaaacaaa tatccatcta accaaccata ttatcaagtt    9420
aagaatattc atgataatta ttttaatgat aataatcaaa caccaatgaa attgaatacg    9480
cgtataccta gcactgatat aagtattatt ccatcttcag caacaatgtg tgaacatata    9540
aaatgctcag ataattctga tttggcaaat agaacagatt tattatgtaa tgggtctcag    9600
cctggaaata atgtgccttt aaatataata aatagcaact caagtagcag caacggaatt    9660
agtaataaaa acattggttt gaatagtagt agtcaccta acaacgtggg aggcatgatt    9720
gttggaggta tgaattcgag taataacaat catataataa ataattttgc ccataaaggt    9780
ggcgaagaag gcgataaatt tactccattt tcttatggag ctttacaaaa taataagtac    9840
gtttctccaa gtcaggggaa taatcaaata tattataata aagcacctat atatgagtca    9900
ccagacattg cttcaaataa aattggaggg aataatacga tgaatactta taattctaga    9960
tctgcagata tttcttcgaa ttattttaac tcaagacttt tacattcgct aagtaacagt   10020
aataatctta ataatgttaa tttaaatgtt gataaaaacg gatattctgc taatatgaga   10080
gatcatatag gaatttcaag acgctcatca acatccatat tatgttcaga gacaaatgaa   10140
aataacgaaa atgtgatttt tatgaaatca agatctccaa gtaattatcc ttcaccatat   10200
aatcccaata agggaataat gcatgataat gatagctcaa aatcctatta cgattcacaa   10260
atattgcaac aacatatgca acaccaaaca catcaatcgg cgcagcaaca atcccaaata   10320
attagcaaca cagatatagt gaataatatg gccatgagta ctaacaacgg tttgaccaat   10380
aacaaagagg aatcgaataa cgaccectca aatatttctg aggcaaaaaa caaaaatgtt   10440
atttatcaga attatgcatt gaataaaatac ccaagcaata gtgtaaaaaa attaagccaa   10500
attaataatc aaaatgattc aaatatccaa ccaggttatc acaatataaa ttatgatcaa   10560
ataaataata attatatacc tcaaaatcta atgaaaaatc ataatgagtt actatcttca   10620
aataatgata aaaaacaaat ggtttattat cctactcatc ctattcctaa ttttgcaaac   10680
```

| | |
|---|---|
| ataaataacg taccattaga aaacttagat aaacacaata ttgctttttc aaatgagtct | 10740 |
| tttaatagaa atataaatta tctcaatcaa attaatttag taaaattgga ccccgtgtca | 10800 |
| gaaaagaaa atatgaatac gggtgcaaaa atagttggag aaaaagtaca gcatacacaa | 10860 |
| cactcgataa aaaataatac ccaacatagt gatatacata attctatcat agaaaataat | 10920 |
| ttagggcaat caaattacgc agttaatatg attaatggtg gttcattaag tagctcaagc | 10980 |
| aatgtcctta tcgagggaac tccaaataat gatattaatg ctgatgttaa taaccaccat | 11040 |
| aacttatccc atataccatc aatctccatg cagcaatcac aaataaatat cgaccaaaat | 11100 |
| aacaattata tatccaatga acatgaaaga gattcagcaa gccgtatgca atttaccct | 11160 |
| aaaggatctg ccataccagt tccaaatcaa caaaatatta atataaataa tcaaggtatt | 11220 |
| aaatataatg agataaatgt acataatata aaacaaccaa ataatttaaa ttcatatatt | 11280 |
| aaccaagtta attttattgt tcaagtatta aataagaaaa aatgtaatca aacagataat | 11340 |
| ataccaccta atataaatca acaaactatg gggaaatata atgtagatca aacagttgtt | 11400 |
| aatacttaa atttgaaaca gggtaacttt gcgaatccaa acttaagtca accacataat | 11460 |
| aacaatatca tacaaaatgg aaataataat aataataaca tgggattatc tacttatcac | 11520 |
| acacaaccaa atacaaattt gaaaaacata aaaccaccaa tgaatgatag caatatatca | 11580 |
| aatatgctca atatgggtat gagaaacaat atgtctaaaa atattatatc aaatattcct | 11640 |
| ccaaataatg tattctcggc taagatgtg attcaacaga aaatactaca acaacaacag | 11700 |
| cataaaatgc aacaagaatt aattcataaa tctcataatg ataaagataa tctagtaaat | 11760 |
| ccacggatgc aatttttctga agaacaaatg cagcaccaaa aattattgca aaaaatgaaa | 11820 |
| caagaacaat tgcaaaaacc gttacaacag attcatccac atcaaatgca aacacacaac | 11880 |
| atgaattcgc aacagcatat gtatattcac ccaatgcaac aaaaaatgca agctctacaa | 11940 |
| atacaatccc ttctaaaagc ccaacagata aaaaaacaat tacacccaag ccaattacaa | 12000 |
| caacaacata tgcaacagaa attacacca cagcaaattc atccgcaaca gttgcgctca | 12060 |
| ccgcaaatac ctcaacaaca gataacacca caacaaatac aacaaataca acaaatgaaa | 12120 |
| atgcataata tacaattcaa gaagcatgaa atgaagaaac atatggagca tttgcaaaaa | 12180 |
| aatataccat ataaccaaca acaaattcat caaatatata atttgcaaca aaatataata | 12240 |
| agtaatgatg aaacaaatga taaacaaaat atgcatctcc aaattagtat gggtataaac | 12300 |
| cccaaaattc aaaatatgca tatgctacaa gcaaaaaata acgatgaatt aatttcaaag | 12360 |
| gagaatttaa ataataattt aaatgaaaat cctatatatg cagtaaatcg aacattttca | 12420 |
| aataatataa ataaatttaa aaatcctgat aattttatt ctcaaaattc ctttcaccca | 12480 |
| actccatcat caaataaaat ggatttaaaa gatattagaa gtataggaaa taaaacatta | 12540 |
| attgaaaata atatcgcatt aaacccttct cagaaaagag cggatatatc taataataac | 12600 |
| attgcacctc atatttacc tattaacatg gcatcatata attctcaaaa tatgcaatgt | 12660 |
| aaaataaata ttaataagaa taatagcaat tcacaagaaa ataattgttg a | 12711 |

<210> SEQ ID NO 9
<211> LENGTH: 42
<212> TYPE: DNA
<213> ORGANISM: Plasmodium berghei

<400> SEQUENCE: 9

| | |
|---|---|
| atttcacata atcataatga tcatataatg gaagaagatg ta | 42 |

<210> SEQ ID NO 10
<211> LENGTH: 42
<212> TYPE: DNA
<213> ORGANISM: Plasmodium berghei

<400> SEQUENCE: 10
atgaaaaagg gaccacaaaa aaatagtgct gataatgctg at                           42

<210> SEQ ID NO 11
<211> LENGTH: 42
<212> TYPE: DNA
<213> ORGANISM: Plasmodium berghei

<400> SEQUENCE: 11
ccaccaaaaa aaagagcttc tagacgtaag ctaaacaaag aa                           42

<210> SEQ ID NO 12
<211> LENGTH: 42
<212> TYPE: DNA
<213> ORGANISM: Plasmodium berghei

<400> SEQUENCE: 12
aatttaacaa gaaaaaaaca aaaagcatca gataataaat gt                           42

<210> SEQ ID NO 13
<211> LENGTH: 39
<212> TYPE: DNA
<213> ORGANISM: Plasmodium berghei

<400> SEQUENCE: 13
gaattccata tgatgatttc cataaccac aacgaccat                                39

<210> SEQ ID NO 14
<211> LENGTH: 39
<212> TYPE: DNA
<213> ORGANISM: Plasmodium berghei

<400> SEQUENCE: 14
gaactgcagt caaagttcat ccttatgatg atggtggtg                               39

<210> SEQ ID NO 15
<211> LENGTH: 38
<212> TYPE: DNA
<213> ORGANISM: Artificial Sequence
<220> FEATURE:
<223> OTHER INFORMATION: PbCap93+Vector

<400> SEQUENCE: 15
ttctacaact acacatatgg gattcgtgct tttctctc                                38

<210> SEQ ID NO 16
<211> LENGTH: 38
<212> TYPE: DNA
<213> ORGANISM: Artificial Sequence
<220> FEATURE:
<223> OTHER INFORMATION: PbCap93+vector

<400> SEQUENCE: 16
cttcatcttc ataagagctc tcaaagttca tccttatg                                38

<210> SEQ ID NO 17
<211> LENGTH: 34
<212> TYPE: DNA
<213> ORGANISM: Artificial Sequence
<220> FEATURE:

```
<223> OTHER INFORMATION: PbCap93+vector

<400> SEQUENCE: 17
ctctcactct tgcagggcta tttcccataa ccac                              34

<210> SEQ ID NO 18
<211> LENGTH: 38
<212> TYPE: DNA
<213> ORGANISM: Artificial Sequence
<220> FEATURE:
<223> OTHER INFORMATION: Pbcap93+vector

<400> SEQUENCE: 18
cttcatcttc ataagagctc tcaaagttca tccttatg                          38
```